US012016960B2

(12) United States Patent
Flaherty et al.

(10) Patent No.: US 12,016,960 B2
(45) Date of Patent: Jun. 25, 2024

(54) ULTRAVIOLET HAND SANITIZER

(71) Applicant: Sloan Valve Company, Franklin Park, IL (US)

(72) Inventors: Thomas Flaherty, Lunenburg, MA (US); Johannes Verzijl, Winthrop, MA (US); Joseph Collins, Worcester, MA (US); Warren Friedl, Chicago, IL (US)

(73) Assignee: Sloan Valve Company, Franklin Park, IL (US)

( * ) Notice: Subject to any disclaimer, the term of this patent is extended or adjusted under 35 U.S.C. 154(b) by 477 days.

(21) Appl. No.: 17/465,310

(22) Filed: Sep. 2, 2021

(65) Prior Publication Data
US 2022/0062454 A1 Mar. 3, 2022

Related U.S. Application Data

(60) Provisional application No. 63/189,919, filed on May 18, 2021, provisional application No. 63/073,767, filed on Sep. 2, 2020.

(51) Int. Cl.
*A61L 2/00* (2006.01)
*A61L 2/10* (2006.01)
*A61L 2/24* (2006.01)
*A61L 2/26* (2006.01)

(52) U.S. Cl.
CPC ......... *A61L 2/0047* (2013.01); *A61L 2202/11* (2013.01); *A61L 2202/14* (2013.01)

(58) Field of Classification Search
CPC ..... A61L 2/26; A61L 2/10; A61L 2/24; A61L 2/0047; A61L 2202/11; A61L 2202/14
See application file for complete search history.

(56) References Cited

U.S. PATENT DOCUMENTS 4,670,010 A * 6/1987 Dragone ................ A61H 35/00
604/289
4,942,631 A * 7/1990 Rosa ........................ E03C 1/057
4/623

(Continued)

FOREIGN PATENT DOCUMENTS

WO 2007051141 A2 5/2007

OTHER PUBLICATIONS

Nov. 26, 2021—(WO) ISR and WO—App PCT/US2021/048848.
Mar. 16, 2023—(WO) IPRP—App PCT/US2021/048848.

*Primary Examiner* — Sean M Luck
(74) *Attorney, Agent, or Firm* — Banner & Witcoff, Ltd.

(57) ABSTRACT

A hand sanitizing device described herein allows users to sanitize and/or disinfect their hands by bathing them in ultraviolet light. The hand sanitizing device may comprise a cabinet that comprises one or more cavities for a user's hands. The one or more cavities may comprise a sensor to detect a user's hands, a controller to send signals to a plurality of ultraviolet lights, and a plurality of ultraviolet lights. Based on a determination that the user has placed their hands in the one or more cavities, the plurality of ultraviolet lights may be illuminated to sanitize and/or disinfectant the user's hands. When the user has removed their hands from the one or more cavities, the plurality of ultraviolet lights may be turned off. By using ultraviolet light, the hand sanitizing device may reduce the spread of infectious diseases and waste consumption associated with bathroom usage.

21 Claims, 18 Drawing Sheets

(56) References Cited

U.S. PATENT DOCUMENTS

| | | | | |
|---|---|---|---|---|
| 5,186,360 A * | 2/1993 | Mease | A47K 5/122 | 222/63 |
| 5,522,411 A * | 6/1996 | Johnson | A47K 10/48 | 134/107 |
| 6,254,625 B1 * | 7/2001 | Rosenthal | A61N 5/0624 | 607/90 |
| 6,431,189 B1 * | 8/2002 | Deibert | A61L 2/22 | 604/289 |
| 6,706,243 B1 * | 3/2004 | Sias | A61L 2/14 | 604/289 |
| 7,118,589 B2 * | 10/2006 | Vlahos | A61N 5/0614 | 607/94 |
| 7,989,779 B1 * | 8/2011 | Ray | A61L 2/10 | 250/493.1 |
| 8,696,161 B2 * | 4/2014 | Pan | F26B 19/00 | 362/249.02 |
| 8,999,261 B2 * | 4/2015 | Benedetto | A61L 2/22 | 422/305 |
| 9,439,988 B2 * | 9/2016 | Troner | A61L 2/06 | |
| 9,517,284 B1 * | 12/2016 | Stibich | A61L 9/18 | |
| 9,649,398 B1 * | 5/2017 | York | E05B 1/0069 | |
| 9,744,255 B2 * | 8/2017 | Stibich | A61L 2/10 | |
| 9,756,989 B2 * | 9/2017 | Ophardt | H02J 7/0013 | |
| 9,761,079 B1 * | 9/2017 | Lin | G07F 13/025 | |
| 10,335,508 B2 * | 7/2019 | Cosman | F26B 3/04 | |
| 2006/0041197 A1 * | 2/2006 | Ophardt | G07F 9/02 | 600/437 |
| 2006/0171843 A1 | 8/2006 | Spears | A61L 2/24 | 422/292 |
| 2006/0186358 A1 * | 8/2006 | Couvillion | A61L 2/10 | 250/504 R |
| 2007/0222554 A1 * | 9/2007 | Hart | G07C 9/25 | 340/5.6 |
| 2007/0255266 A1 * | 11/2007 | Cumbie | A61N 5/0624 | 606/9 |
| 2008/0199354 A1 * | 8/2008 | Gordon | A61L 2/10 | 422/186.3 |
| 2009/0299787 A1 * | 12/2009 | Barnhill | G08B 21/245 | 434/365 |
| 2009/0314308 A1 * | 12/2009 | Kim | A61L 2/0088 | 134/1 |
| 2010/0252569 A1 * | 10/2010 | Pelfrey | A47K 5/12 | 136/246 |
| 2010/0266446 A1 | 10/2010 | Constantacos | | |
| 2010/0293805 A1 * | 11/2010 | Chang | A45D 29/00 | 34/202 |
| 2011/0303694 A1 * | 12/2011 | Pie | B65D 33/00 | 222/137 |
| 2012/0085780 A1 * | 4/2012 | Landauer | A47K 5/12 | 222/105 |
| 2012/0153783 A1 * | 6/2012 | Shoenfeld | A61L 2/10 | 362/133 |
| 2012/0305804 A1 * | 12/2012 | Goldman | E05B 1/0069 | 250/492.1 |
| 2013/0187779 A1 * | 7/2013 | Pokrajac | G08B 21/18 | 340/573.1 |
| 2013/0256560 A1 * | 10/2013 | Yerby | A61L 2/24 | 250/455.11 |
| 2014/0172523 A1 * | 6/2014 | Stob | A47K 5/1217 | 222/25 |
| 2014/0252247 A1 * | 9/2014 | Moskowitz | A61L 2/10 | 250/492.1 |
| 2015/0209457 A1 | 7/2015 | Bonutti et al. | | |
| 2016/0000951 A1 * | 1/2016 | Kreiner | A61L 2/0047 | 250/492.1 |
| 2016/0030766 A1 * | 2/2016 | Scritchfield | G06V 40/107 | 607/91 |
| 2016/0158395 A1 * | 6/2016 | Hughes | A61L 2/10 | 250/455.11 |
| 2016/0367712 A1 * | 12/2016 | Robert | A61L 9/22 | |
| 2017/0006993 A1 * | 1/2017 | Rivero | A45D 29/00 | |
| 2017/0165387 A1 * | 6/2017 | Robert | H05K 5/0004 | |
| 2017/0246332 A1 * | 8/2017 | Marshall | E05B 1/0069 | |
| 2018/0117191 A1 * | 5/2018 | Shell | B65B 55/02 | |
| 2018/0221520 A1 * | 8/2018 | Nguyen | A61L 2/24 | |
| 2018/0280554 A1 * | 10/2018 | Khajavi | A61L 2/10 | |
| 2018/0321153 A1 * | 11/2018 | Llamido | G01N 21/6447 | |
| 2018/0357886 A1 * | 12/2018 | Tavori | G16H 40/20 | |
| 2019/0117802 A1 * | 4/2019 | Hishinuma | B01J 21/063 | |
| 2019/0192705 A1 * | 6/2019 | Masyk | A61L 2/18 | |
| 2019/0321499 A1 | 10/2019 | Igarashi | | |
| 2020/0121818 A1 * | 4/2020 | Kaneko | F24F 7/06 | |
| 2020/0261608 A1 | 8/2020 | Crosby et al. | | |
| 2022/0175997 A1 * | 6/2022 | Kolakowski | A61L 2/0047 | |

* cited by examiner

1  DIM LIGHT DRAWS YOU IN.

2  LIGHTS COMPLETE A 3 SECOND ORBIT.

3  BRIGHT FLASH INDICATES CYCLE IS FINISHED.

ULTRAVIOLET HAND SANITIZER

CROSS-REFERENCE TO RELATED APPLICATIONS

This application is a nonprovisional of, and claims priority to, U.S. Provisional Application No. 63/073,767, filed on Sep. 2, 2020, and entitled "Ultraviolet Hand Sanitizer," and U.S. Provisional Application No. 63/189,919, filed on May 18, 2021, and entitled "Ultraviolet Hand Sanitizer," both of which prior applications are incorporated herein by reference in their entireties.

FIELD OF THE DISCLOSURE

Aspects of the disclosure generally relate to a hand sanitization device and more specifically to a bathroom fixture for sanitizing hands using ultraviolet light.

BACKGROUND OF THE DISCLOSURE

According to the Center for Disease Control (CDC), the most effective hand sanitizing method comprises washing and scrubbing hands with soap and water and then drying the hands, either via a hand towel or automatic hand dryers. Additionally, hand sanitizers (e.g., Purell® hand sanitizer) have become popular as either a supplement to hand washing or as a substitute to a comprehensive hand wash when soap and water are not available. Replacing hand-washing and/hand sanitizers faces a number of problems, including effective sanitization/disinfecting, providing power for sanitization stations, and/or reducing the bacterial count on a hand surface in a reasonable exposure time.

BRIEF SUMMARY OF THE DISCLOSURE

The following presents a simplified summary of various aspects described herein. This summary is not an extensive overview, and is not intended to identify key or critical elements or to delineate the scope of the claims. The following summary merely presents some concepts in a simplified form as an introductory prelude to the more detailed description provided below. Corresponding apparatus, systems, methods, and computer-readable media are also within the scope of the disclosure.

The present disclosure describes a hand sanitizing device that may allow users to sanitize and/or disinfect their hands by bathing a user's hands in a bath of ultraviolet light. The hand sanitizing device may comprise a body. The body may be wall-mounted and include an electrical connection to connect to a power source. The body may comprise one or more cavities for receiving a user's hands. The body may further comprise one or more sensors, one or more microcontrollers, and a plurality of ultraviolet lights associated with the one or more cavities. The one or more sensors may be configured to detect when a user places their hands into and/or removes their hands from the one or more cavities, and may be, for example, proximity sensors. Based on a determination that the user has placed their hands in the one or more cavities, the one or more sensors may send (e.g., transmit) a signal to the one or more microcontrollers. The microcontroller(s) may send (e.g., transmit) a signal to the plurality of ultraviolet lights to turn on the plurality of ultraviolet lights, for example, based on or in response to the signal received from the one or more sensors. Similarly, the one or more sensors may be configured to detect when the user has removed their hands from the one or more cavities.

The one or more sensors may send (e.g., transmit) a signal to the microcontroller(s) indicating that the user has removed their hands from the one or more cavities. The microcontroller(s_ may then send (e.g., transmit) another signal to turn off the plurality of ultraviolet lights, for example, based on or in response to the signal received from the one or more sensors. The microcontroller(s) may also be configured to turn the ultraviolet lights off after a set period of time after activation.

In some instances, the hand sanitizing device may comprise one or more indicators, such as light emitting diodes (LEDs) or a liquid crystal display (LCD) monitor or other visual indicator(s). The one or more indicators may provide the user with instructions on using the hand sanitizing device. For instance, LEDs may provide a first indication that signals that the device is in standby mode and/or waiting for a user to insert their hands. A second indication may provide an indication that the sanitation and/or disinfection process is in progress. In some examples, the second indication may provide a countdown until the sanitation and/or disinfection process is completed. The third indication may indicate that the sanitation and/or disinfection process has been completed. In another example, the LCD monitor may cause the status of the sanitation and/or disinfection process to be displayed on the LCD monitor. These indications may be designed to be easily understood by and clearly communicate to users the status of the sanitation and/or disinfection process.

The hand sanitizing device described herein may sanitize hands without any liquids, such as soap and water or hand sanitizing fluids. Accordingly, the hand sanitizing device described herein may reduce the spread of infectious diseases, while providing an environmentally friendly solution that reduces water consumption and/or further reduces waste associated with drying towels.

Aspects of the disclosure relate to a hand sanitizing device that includes a supporting body having a space configured to receive one or more hands of a user, the supporting body having a first surface and a second surface, with the space defined between the first and second surfaces, such that the first and second surfaces face into the space and are in confronting relation with each other. The first surface and the second surface are angled at an acute angle (e.g., 10-30 degrees) with respect to each other. A sensor is mounted on the supporting body and directed into the space, and the sensor is configured for sensing a presence of the one or more hands of the user within the space. A first light array including a first plurality of light emitting devices is mounted on the supporting body and configured to emit ultraviolet light from the first surface into the space, and a second light array including a second plurality of light emitting devices is mounted on the supporting body and configured to emit ultraviolet light from the second surface into the space. A controller is mounted on the supporting body and connected to the sensor and the first and second light arrays, and the controller is configured to receive input from the sensor and to activate the first and second light arrays when the presence of the one or more hands of the user within the space is sensed by the sensor.

According to one aspect, the supporting body has a second space configured to receive one or more hands of a user, the supporting body having a third surface and a fourth surface, with the second space defined between the third and fourth surfaces, such that the third and fourth surfaces face into the second space and are in confronting relation with each other.

According to another aspect, the sensor is an infrared sensor including one or more infrared transmitters and one or more infrared receivers. In one configuration, the sensor may be a time of flight sensor.

According to a further aspect, the ultraviolet light emitted by the first plurality of light emitting devices and the second plurality of light emitting devices has a wavelength of 222 nm.

According to yet another aspect, the device also includes a visual indicator mounted on the supporting body and configured to display a visual indication to the user related to operation of the hand sanitizing device.

According to a still further aspect, the first light array further includes a first filter positioned over the first plurality of light emitting devices and the second light array further includes a second filter positioned over the second plurality of light emitting devices, where the first and second filters limit the wavelength of the ultraviolet light passing through the first and second filters, e.g., to 222 nm.

Additional aspects of the disclosure relate to a hand sanitizing device that includes a supporting body having a lower portion with a first surface and an upper portion with a second surface, with a space configured to receive one or more hands of a user, the space being defined between the first and second surfaces, such that the first and second surfaces face into the space and are in confronting relation with each other. The supporting body further includes an arm connecting the lower portion to the upper portion and extending vertically from the lower portion to the upper portion. A sensor is mounted on the supporting body and directed into the space, and the sensor is configured for sensing a presence of the one or more hands of the user within the space. A first light array including a first plurality of light emitting devices is mounted on the lower portion and configured to emit ultraviolet light from the first surface into the space, and a second light array including a second plurality of light emitting devices is mounted on the upper portion and configured to emit ultraviolet light from the second surface into the space. A controller is mounted on the supporting body and connected to the sensor and the first and second light arrays, where the controller is configured to receive input from the sensor and to activate the first and second light arrays when the presence of the one or more hands of the user within the space is sensed by the sensor.

According to one aspect, the first surface and the second surface are angled at an acute angle with respect to each other.

According to another aspect, the first surface and the second surface are angled at an acute angle with respect to each other. In one configuration, the acute angle may be from 10 degrees to 30 degrees.

According to a further aspect, a visual indicator is mounted on the supporting body and configured to display a visual indication to the user related to operation of the hand sanitizing device.

According to a still further aspect, the ultraviolet light emitted by the first plurality of light emitting devices and the second plurality of light emitting devices has a wavelength of 222 nm, where the first light array includes a first filter positioned over the first plurality of light emitting devices and the second light array includes a second filter positioned over the second plurality of light emitting devices, and wherein the first and second filters limit the wavelength of the ultraviolet light passing through the first and second filters to 222 nm.

According to yet another aspect, the upper portion and the lower portion have circular cylindrical shapes, and/or the sensor is mounted on the arm and is directed into the space.

Further aspects of the disclosure relate to a hand sanitizing device including a supporting body that includes a lower portion including a vertically-elongated cylindrical column having a top surface, an upper portion including a vertically-elongated cylindrical column having a bottom surface positioned directly above the top surface of the lower portion, and an arm connecting the lower portion to the upper portion and extending vertically from the lower portion to the upper portion. A space is defined between the top and bottom surfaces, such that the top and bottom surfaces face into the space and are in confronting relation with each other. The space is configured to receive one or more hands of a user, and the top surface and the bottom surface are angled at acute angles with respect to a horizontal plane. A first light emitting device is mounted on the lower portion and configured to emit ultraviolet light from the top surface into the space, and a second light emitting device is mounted on the upper portion and configured to emit ultraviolet light from the bottom surface into the space. A sensor is directed into the space, the sensor being configured for sensing a presence of the one or more hands of the user within the space.

According to one aspect, the sensor is mounted on the arm and is directed into the space.

According to an additional aspect, a controller is mounted on the supporting body and connected to the sensor and the first and second light emitting devices, where the controller is configured to receive input from the sensor and to activate the first and second light emitting devices when the presence of the one or more hands of the user within the space is sensed by the sensor.

According to another aspect, a first filter is positioned over the first light emitting device and a second filter is positioned over the second light emitting device. The first and second filters limit a wavelength of the ultraviolet light passing through the first and second filters. The first filter forms a portion of the top surface, and the second filter forms a portion of the bottom surface.

According to a further aspect, the top surface and the bottom surface are angled at an acute angle of 10 degrees to 30 degrees with respect to each other.

Other features and advantages of the disclosure will be apparent from the following description taken in conjunction with the attached drawings.

BRIEF DESCRIPTION OF THE DRAWINGS

The present disclosure is described by way of example and not limited in the accompanying figures in which.

DETAILED DESCRIPTION OF THE DISCLOSURE

Figure 1:
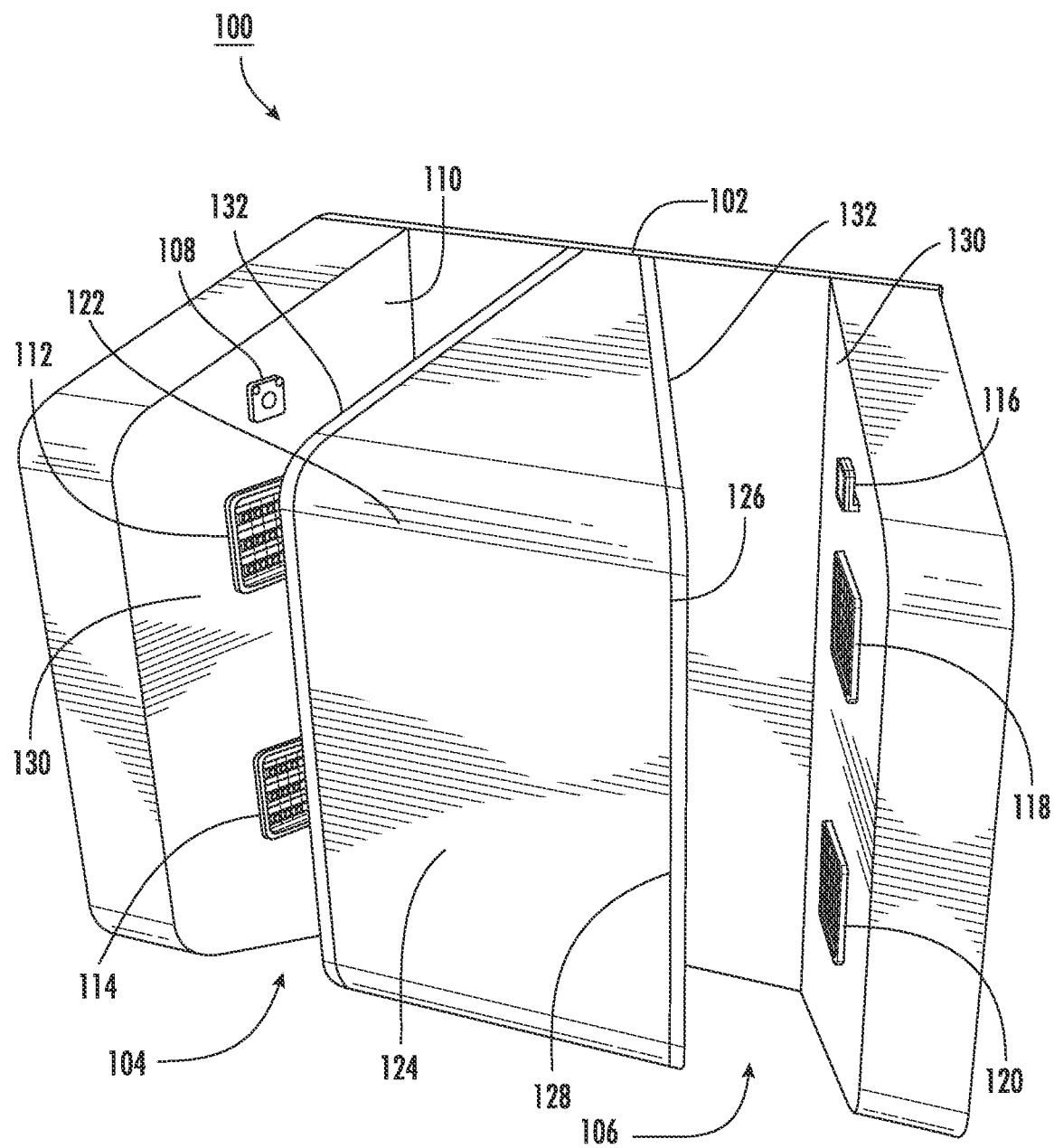
FIG. 1 shows an example of a hand sanitizing device according to one or more aspects of the disclosure.

In the following description of the various example embodiments, reference is made to the accompanying drawings, which form a part hereof, and in which is shown by way of illustration various example embodiments in which aspects of the disclosure may be practiced. It is to be understood that other embodiments may be utilized and structural and functional modifications may be made without departing from the scope of the present disclosure. Aspects of the disclosure are capable of other embodiments and of being practiced or being carried out in various ways. In addition, it is to be understood that the phraseology and terminology used herein are for the purpose of description and should not be regarded as limiting. Rather, the phrases and terms used herein are to be given their broadest interpretation and meaning.

The COVID-19/coronavirus pandemic has driven consumers to seek touchless and/or non-consumable hand sanitizing regimes. However, most touchless and/or non-consumable solutions face several challenges, including limited to no power availability and/or a long exposure time to significantly reduce the bacterial count on a surface of the user's hands.

By way of introduction, aspects discussed herein may describe a hand sanitizing device that may allow users to sanitize and/or disinfect their hands using ultraviolet light. The hand sanitizing device may comprise one or more cavities for a user's hands. The device may comprise one or more sensors and/or a plurality of ultraviolet lights associated with each of the one or more cavities, and may further include one or more microcontrollers in communication with the sensor(s) and/or the lights. The one or more sensors may be configured to detect when a user's hands are inserted into and/or removed from the one or more cavities. The one or more sensors may send (e.g., transmit) a signal to the one or more microcontrollers, for example, based on a determination that the user has placed their hands in the one or more cavities. In response to the signal received from the one or more sensors, the one or more microcontrollers may send (e.g., transmit) a signal to the plurality of ultraviolet lights to turn on the plurality of ultraviolet lights to sanitize and/or disinfect the user's hands. When the user removes their hands, the one or more sensors may send (e.g., transmit) a signal to the microcontroller indicating the removal. The one or more microcontrollers may, in turn, send (e.g., transmit) another signal to turn off the plurality of ultraviolet lights. The microcontroller(s) may also be configured to turn the ultraviolet lights off after a set period of time after activation.

In another embodiment, the device may additionally or alternately include a manual activation mechanism, which can activate and/or deactivate the lights in response to user input. For example, the device may include a button to activate the lights, and the lights may be deactivated automatically after a set period of time.

Additionally, the present disclosure may describe processes, methods, and techniques for how to use the hand sanitizing device described herein. For example, the hand sanitizing device may provide a first indication, to a user, that signals that the device is in standby mode and/or waiting for a user to insert their hands. Once a user has inserted their hands into the hand sanitizing device, a second indication may be provided to the user. The second indication may signal that the sanitation and/or disinfection process is in progress. Additionally or alternatively, the second indication may comprise a countdown until the sanitation and/or disinfection process is completed. Finally, the hand sanitizing device may provide a third indication to the user, which may indicate that the sanitation and/or disinfection process has been completed.

The hand sanitizing device described herein may sanitize hands without any liquids, such as soap and water or hand sanitizing fluids. Accordingly, the hand sanitizing device described herein may reduce the spread of infectious diseases, while providing an environmentally friendly solution that reduces water consumption and/or further reduces waste associated with drying towels.

Turning to FIG. 1, an example of a hand sanitizing device 100 according to one or more aspects of the disclosure. Hand sanitizing device may comprise a supporting body 102 in the form of a cabinet. Body 102 may be wall-mounted or free-standing, or may be configured for use as either a wall-mounted or free-standing unit. Body 102 may be modeled off a hand dryer experience, in which hand sanitizing can be accomplished by simple hand presentation with a device containing multiple planar openings. Body 102 may comprise at least one space or cavity, such as a first space or cavity 104 and a second space or cavity 106. The cavity or cavities 104, 106 may be configured to receive a user's hands for sanitation/disinfection. As shown in FIG. 1, body 102 may be W-shaped, providing vertically oriented cavities 104, 106 for the user's hands. In this regard, vertical cavities may allow a degree of movement, which may reduce a user's desire to fidget. Additionally, vertical cavities may remove the need to drain water which may inadvertently enter a horizontal unit. While FIG. 1 shows body 102 as W-shaped, it will be appreciated that body 102 may be any shape capable of receiving a user's hands, including cylindrical, rectangular, etc. Body 102 may house the electrical components associated with first sensor 108, second sensor 116, processor 110, a first light array 112, a second light array 114, a third light array 118, and a fourth light array 120, a fifth light array 122, a sixth light array 124, a seventh light array 126, and an eighth light array 128. First sensor 108 and/or second sensor 116 may comprise one or more exterior components configured to detect the presence and/or absence of a user's hands. The one or more exterior components may be mounted on the surfaces of the body 102 defining the one or more cavities and exposed via the one or more cavities. Each light array 112, 114, 118, 120, 122, 124, 126, 128 may have one or more exterior facing components mounted on the surfaces of the body 102 defining the one or more cavities and exposed to the one or more cavities. The one or more exterior facing components may comprise one or more light arrays.

In one embodiment, body 102 includes at least a first surface 130 and a second surface 132 defining each of the cavities 104, 106, where the first and second surfaces 130, 132 oppose or confront each other and are oriented to be generally parallel with the palms and backs of the user's hands. Each of the first and second surfaces 130, 132 includes one or more light arrays 112, 114, 118, 120, 122, 124, 126, 128 thereon, such that light is emitted on both sides of the user's hands when inserted into the cavities 104, 106, as shown in FIG. 1. This configuration helps ensure that the light is emitted onto all surfaces of the user's hands as long as the hands remain within the cavities 104, 106. The sensors 108, 116 may have portions that are positioned on one or more of the surfaces 130, 132 as also shown in FIG. 1.

First sensor 108 and second sensor 116 may be any sensor configured to detect human hands being inserted and/or removed from first cavity 104 and second cavity 106, respectively. Additionally or alternatively, first sensor 108 and second sensor 116 may be configured to detect proper hand placement within first cavity 104 and second cavity 106. In some instances, first sensor 108 and/or second sensor 116 may be an infrared (IR) active sensor comprising one or more IR transmitters and one or more IR receivers. For example, first sensor 108 and/or second sensor 116 may be a Sloan® G2 proximity sensor. First sensor 108 and/or second sensor 116 may include a low powered IR diode configured to emit (e.g., transmit, irradiate) IR light at a steady (e.g., constant, continuous) rate. The one or more IR receivers may be one or more photoreceptors configured to detect IR light transmitted by the one or more IR transmitters. In this regard, first sensor 108 and/or second sensor 116 may detect an object proximately located in first cavity 104 and/or second cavity 106 if a certain amount and/or intensity of IR light was detected. For example, if the detected light was equal to or greater than a predetermined threshold (e.g., a predetermined number of lumens), first sensor 108 and/or second sensor 116 may indicate an object is located within first cavity 104 and/or second cavity 106.

Alternatively, first sensor 108 and/or second sensor 116 may comprise a digital proximity, ambient light, RGB, and/or gesture sensor. For example, first sensor 108 and/or second sensor 116 may be a VL53L1CXV0FY/1 Time of Flight (ToF) sensor from STMicroelectronics, which provides a compact package (4.9 mm L×2.5 mm W×1.56 mm H). As another example, first sensor 108 and/or second sensor 116 may be an APDS-9960 device from Avago Technologies. The APDS-9960 may provide a slim modular package (3.94 mm L×2.36 mm W×1.35 mm H). Like the sensors described above, first sensor 108 and/or second sensor 116 may incorporate an IR LED and calibrated LED driver for gesture detection, proximity detection, Digital Ambient Light Sense (ALS), and/or Color Sense (RGBC). The proximity detection feature may provide distance measurement (e.g., user's hand to sensor) by photodiode detection of reflected IR energy (sourced by the integrated LED). The Color and ALS detection feature may provide red, green, blue, and/or clear light intensity data. Each channel (e.g., R, G, B, C channels) may comprise a UV and/or IR blocking filter. Additionally, each channel (e.g., R, G, B, C channels) may comprise a dedicated data converter producing 16-bit data simultaneously. The UV and/or IR blocking filter may allow applications to accurately measure ambient light and/or sense color which enables devices to calculate color temperature and/or control display backlight.

The or each microcontroller may include a processor 110 in communication with the sensors 108, 116 and the light arrays 112, 114, 118, 120, 122, 124, 126, 128. Processor 110 may be may be any suitable processor configured to receive signals associated with the presence and/or absence of a user's hands from first sensor 108 and/or second sensor 116 and send signals to turn on/off one or more of the light arrays 112, 114, 118, 120, 122, 124, 126, 128. Processor 110 may comprise a single central processing unit (CPU), which may be a single-core or multi-core processor, or may include multiple CPUs. Additionally or alternatively, processor 110 may include a low-power processor and/or microcontroller, such as an Advanced RISC Machine (ARM) processor, an Atmel 8-bit AVR microcontroller, an ATmega328 microcontroller, and/or any suitable field programmable array (FPGA) or application specific integrated circuit (ASIC). Processor 110 and/or the associated components described herein may execute a series of computer-readable instructions to perform some or all of the processes described herein. In some examples processor 110 may comprise an internal memory. The memory may be cache, random access memory (RAM), read only memory (ROM), electronically erasable programmable read only memory (EEPROM), flash memory, or other memory technology. The memory may be configured to store the series of computer-readable instructions that allow processor 110 to perform some or all of the processes described herein. While FIG. 1 illustrates one processor, it will be appreciated that the hand sanitizing device 100 may comprise a plurality of processors, and that any suitable processor or combination of processors may be used in connection with the device 100.

Each light array 112, 114, 118, 120, 122, 124, 126, 128 may comprise any suitable light array configured to generate ultraviolet light in a wavelength safe for human tissue. The ultraviolet light generated by each light array 112, 114, 118, 120, 122, 124, 126, 128 may be 222 nm, which has proven effective for killing and/or destroying bacteria and viruses without being dangerous to humans and/or penetrating deeply into human cells. It is understood that the wavelength of the light generated by the light arrays 112, 114, 118, 120, 122, 124, 126, 128 may be controlled by selective emission from the light arrays 112, 114, 118, 120, 122, 124, 126, 128, the use of filters as discussed herein, or both. Alternatively, the ultraviolet light may be 147 nm, 172 nm, 220-280 nm, or 308 nm in wavelength in some embodiments, or 220-250 nm in one embodiment. In some examples, each light array 112, 114, 118, 120, 122, 124, 126, 128 may comprise microplasma ultraviolet lamps, such as those provided by Eden Park. In this regard, each light array 112, 114, 118, 120, 122, 124, 126, 128 may comprise a plurality of ultraviolet light emitting diodes (LEDs). Preferably each of the light arrays 112, 114, 118, 120, 122, 124, 126, 128 may comprise a 50 mm (L)×50 mm (W)×3 mm (H) tile. Alternatively, the plurality of ultraviolet LEDs may be in a 125 mm (L)×50 mm (W)×3 mm (H) tile. The first light array 112 and/or the second light array 114 may be driven by one or more ballasts (not shown). It will be appreciated that some or all of the light arrays 112, 114, 118, 120, 122, 124, 126, 128 may have different geometries from each other. The light arrays 112, 114, 118, 120, 122, 124, 126, 128 may provide illumination of large surface area, which may be defined by the quantity of lamps. Additionally, each light array 112, 114, 118, 120, 122, 124, 126, 128 and/or the microcontroller(s) may comprise internal safety devices so as to not over expose or allow users to repeatedly insert hands without downtime between applications. In some examples, the internal safety device may be designed to generate ultraviolet light in response to detecting only human hands (e.g., via sensors as described herein) as an additional precaution. In some other examples, the internal safety device may include a time-out feature that deactivates the light arrays 112, 114, 118, 120, 122, 124, 126, 128 after a set time period (e.g., 5 seconds) and/or establishes a fixed minimum off-time for the light arrays 112, 114, 118, 120, 122, 124, 126, 128, in order to avoid over-exposure.

Figure 2A:
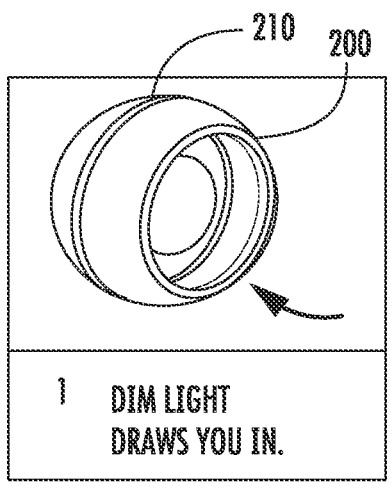
FIGS. 2A-2C shows an example of process for using a hand sanitizing device in accordance with one or more aspects of the disclosure.
Figure 2B:
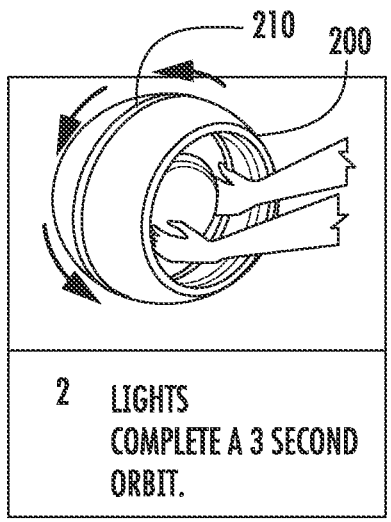
Figure 2C:
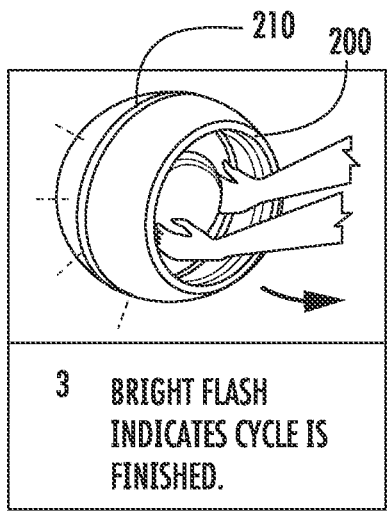

The hand sanitizing device may provide visual cues and/or instructions for how to use the hand sanitizing device. FIGS. 2A-2C shows an example of process for using a hand sanitizing device in accordance with one or more aspects of the disclosure. Some or all of the steps of process may be performed using one or more computing devices as described herein such as hand sanitizing device 100.

FIG. 2A shows an example of a hand sanitizing device 200 comprising a visual indicator 210. The visual indicator 210 may comprise one or more light emitting diodes (LEDs) and/or a display, such as an LCD display or an LED display. The one or more LEDs may surround the perimeter or circumference of hand sanitizing device 200. In FIG. 2A, visual indicator 210 may provide a first indication that hand sanitizing device 200 is ready for use. In this regard, the first indication may comprise a first state of the one or more LEDs. The first state may be a dimmed state of the LEDs that invites a user to use hand sanitizing device 200. Additionally or alternatively, the first indication may comprise causing a message (e.g., "Ready") to be presented on the display.

FIG. 2B shows an example of a user inserting their hands in hand sanitizing device 200. By inserting their hands, the user may cause visual indicator 210 to display a second indication to the user. The second indication may signal that the sanitation and/or disinfection process is in progress. Additionally or alternatively, the second indication may comprise a countdown until the sanitation and/or disinfection process is completed. When visual indicator 210 comprises one or more LEDs, the second indication may comprise a light band that traverses the perimeter (e.g., circumference) of hand sanitizing device 210. The light band may travel around the perimeter more quickly to indicate a countdown until completion of the sanitation and/or disinfection process. Additionally or alternatively, one or more LEDs may blink or change color or intensity to indicate a countdown until completion of the sanitation and/or disinfection process. When visual indicator 210 comprises a display, visual indicator 210 may cause a status of operation and/or a countdown to be displayed. It will be appreciated the visual indicator 210 may comprise both one or more LEDs and/or the display described above and that the status may be conveyed in multiple ways.

FIG. 2C shows an example of the user completing the sanitation and/or disinfection process. Visual indicator 210 may cause a third indication to be presented. The third indication may convey that the sanitation and/or disinfection process has completed. When visual indicator 210 comprises one or more LEDs, the third indication may comprise a sequence or pattern of blinking lights to convey that the sanitation and/or disinfection process has completed. When visual indicator 210 comprises a display, visual indicator 210 may cause a completion status to be presented. As noted above, one or more visual indicators may be used to convey that the sanitation and/or disinfection process has completed. In addition to providing instructions to a user, visual indicator 210 may cause instructions and/or diagnostics to be presented.

Figure 3:
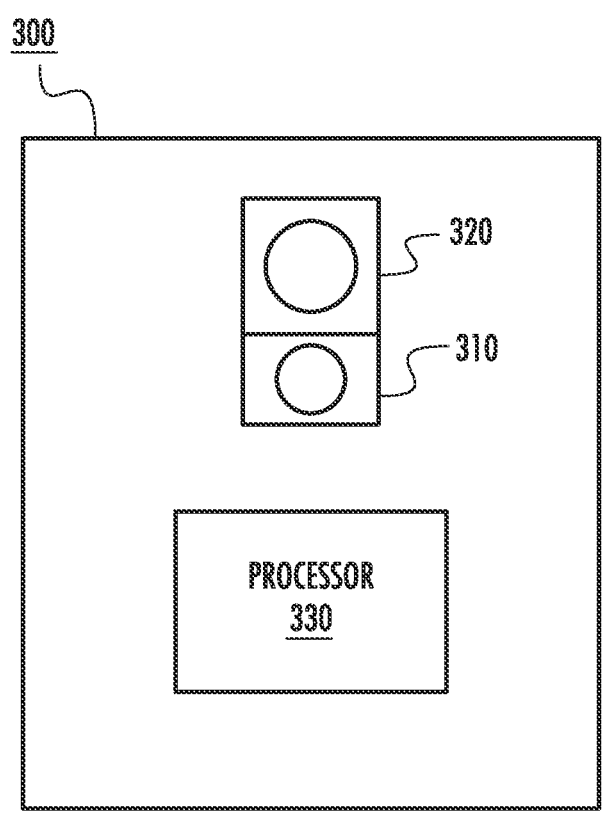
FIG. 3 shows an example of a sensor according to one or more aspects of the disclosure.

FIG. 3 shows an example of a sensor 300 according to one or more aspects of the disclosure. As noted above, sensor 300 may be a VL53L1CXV0FY/1 Time of Flight (ToF) sensor from STMicroelectronics, a Sloan® G2 proximity sensor, and/or an APDS-9960 device from Avago Technologies. Sensor 300 may comprise IR transmitter 310, IR receiver 320, and a microcontroller including a processor 330. IR transmitter 310 may be a low powered IR diode configured to emit (e.g., transmit, irradiate) IR light at a steady (e.g., constant, continuous) rate. In some examples, IR transmitter 310 comprises a plurality of LEDs configured to emit IR light at a particular intensity, frequency, and/or wavelength. IR receiver 320 may be one or more photoreceptor cells. The one or more photoreceptor cells may be configured to detect IR light transmitted by IR transmitter 310. Processor 330 may be any of the processors discussed above with respect to FIG. 1. Processor 330 may be configured to determine if the light detected by IR receiver 320 is equal to or greater than a predetermined threshold (e.g., a predetermined number of lumens). If so, processor 330 may determine that an object is proximately located near sensor 300. Processor 330 may cause a signal to be sent (e.g., transmitted), which may illuminate the first light array 112, second light array 114, third light array 118, fourth light array 120, fifth light array 122, sixth light array 124, seventh light array 126, and/or eighth light array 128. If the detected light is below the threshold, processor 330 may determine that an object is not proximate to sensor 300. If a light array 112, 114, 118, 120, 122, 124, 126, 128 is in an illuminated state, processor 330 may cause a signal to be sent (e.g., transmitted) to turn off the respective light array 112, 114, 118, 120, 122, 124, 126, 128. If a light array 112, 114, 118, 120, 122, 124, 126, 128 is not in an illuminated state, then processor 330 may not send any signal.

Figure 4A:
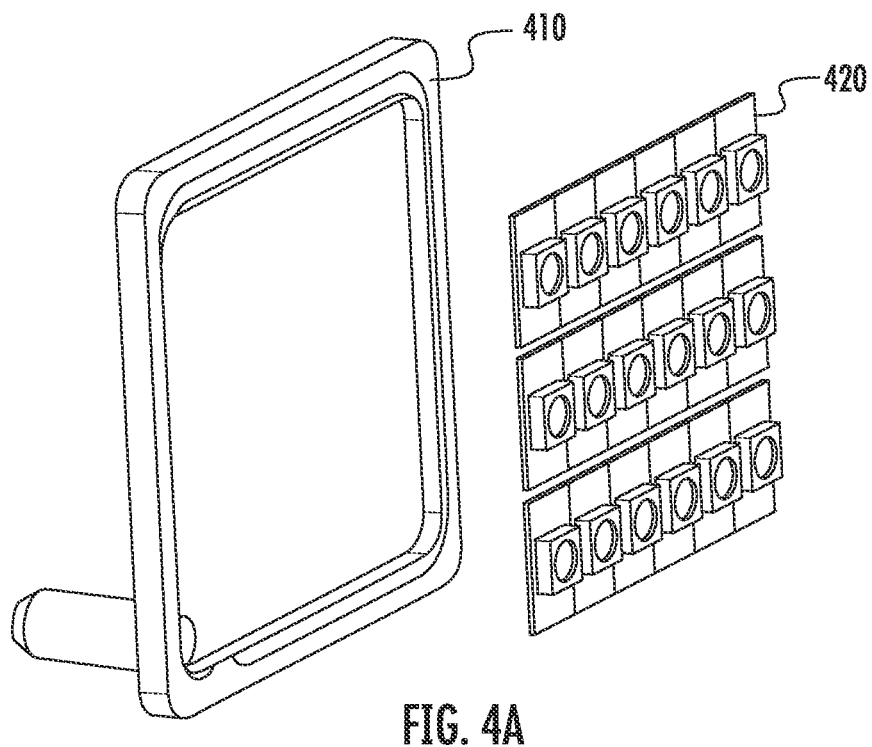
FIGS. 4A and 4B show an example of light array assembly in accordance with one or more aspects of the disclosure.
Figure 4B:
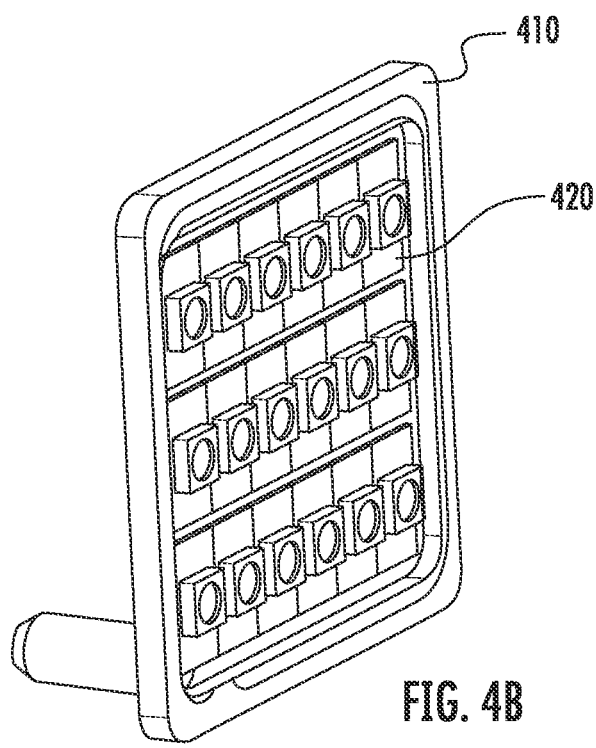

FIGS. 4A and 4B show an example of light array assembly in accordance with one or more aspects of the disclosure. The light array assembly may comprise a socket 410 and a light array 420 formed of a plurality of light emitting devices (e.g., LED's) arranged within the socket 410. The light array 420 may comprise any suitable light array configured to generate ultraviolet light. The ultraviolet light may be of a wavelength safe for human tissue and effective for sanitizing. Preferably, the wavelength of the ultraviolet light generated by the light array 420 is 222 nm, which has proven effective for killing and/or destroying bacteria and viruses without being dangerous to humans and/or penetrating deeply into human cells. In other embodiments, the ultraviolet light generated by the light array 420 has a different wavelength as described herein. It is understood that the wavelength of the light generated by the light array 420 may be controlled by selective emission from the light array 420, the use of filters as discussed herein, or both. The socket 420 may be a 50 mm (L)×50 mm (W)×3 mm (D) square tile. This may allow for the use of multiple sockets and/or light arrays to illuminate an area. While a square tile is shown, it will be appreciated that the socket 410 and/or light array 420 may have different geometries (e.g., rectangular, hexagonal, octagonal, etc.) Socket 410 and/or light array 420 may comprise a safety mechanism to limit a user's exposure to ultraviolet light as described herein.

Figure 5A:
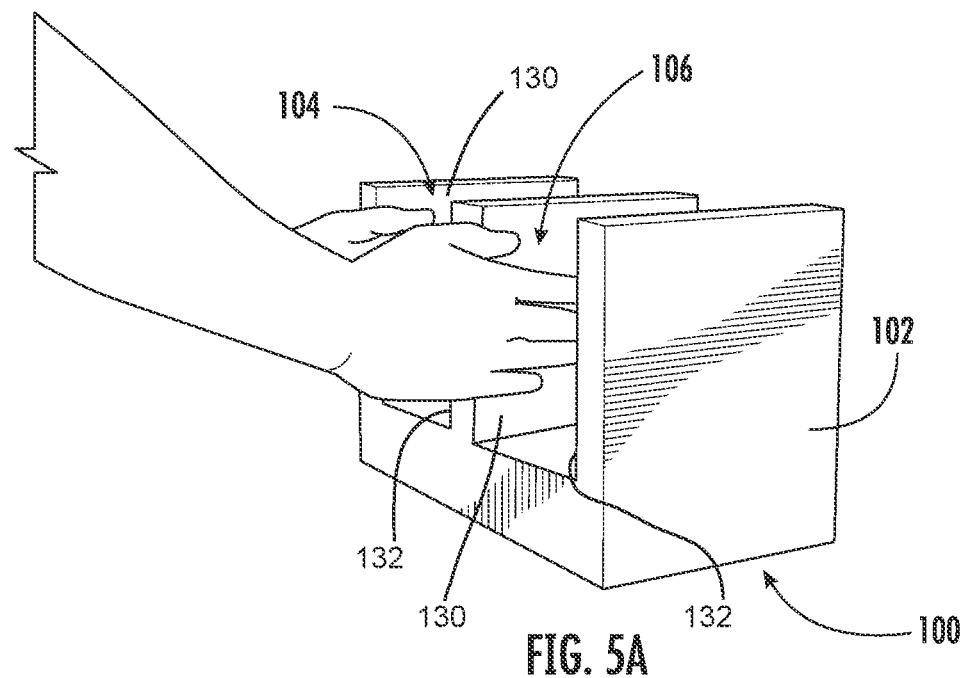
FIGS. 5A-5P show additional examples of hand sanitizing devices according to one or more aspects of the disclosure.
Figure 5B:
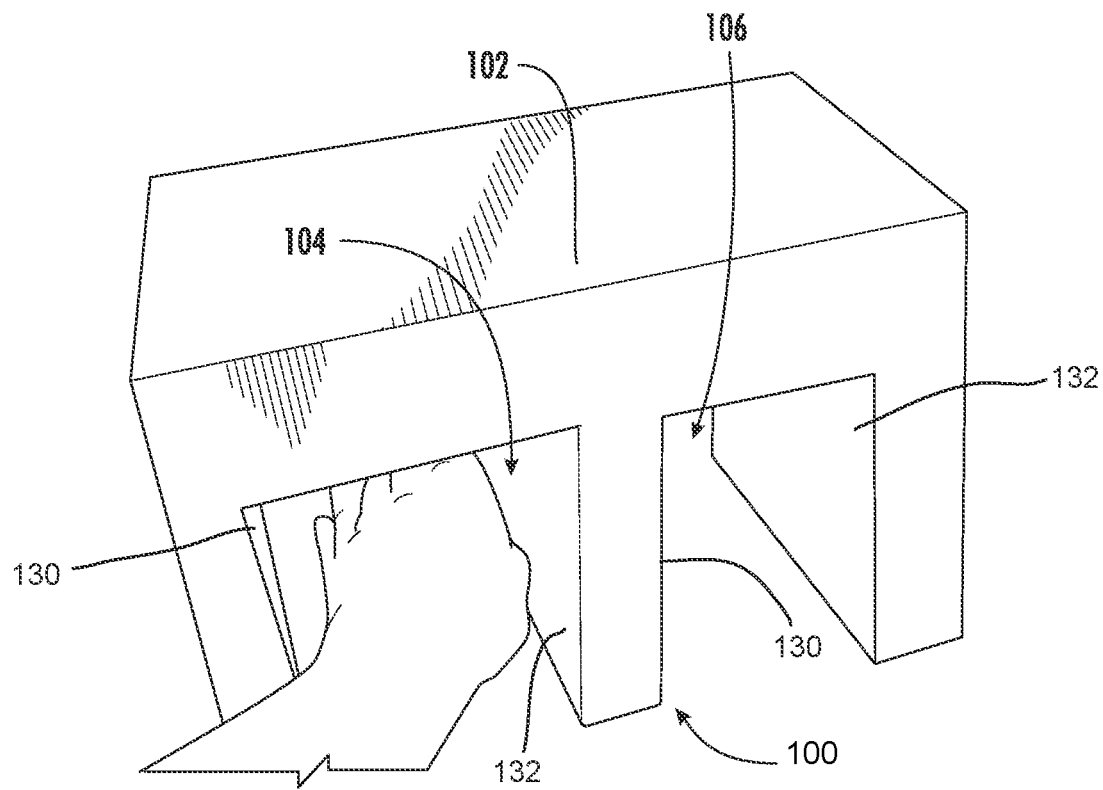
Figure 5C:
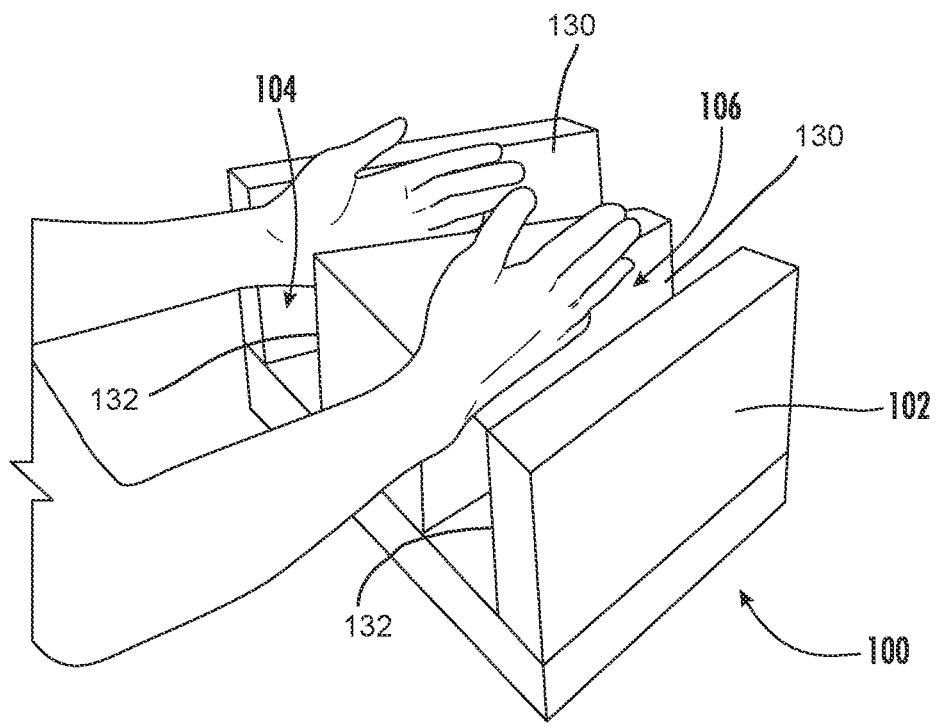
Figure 5D:
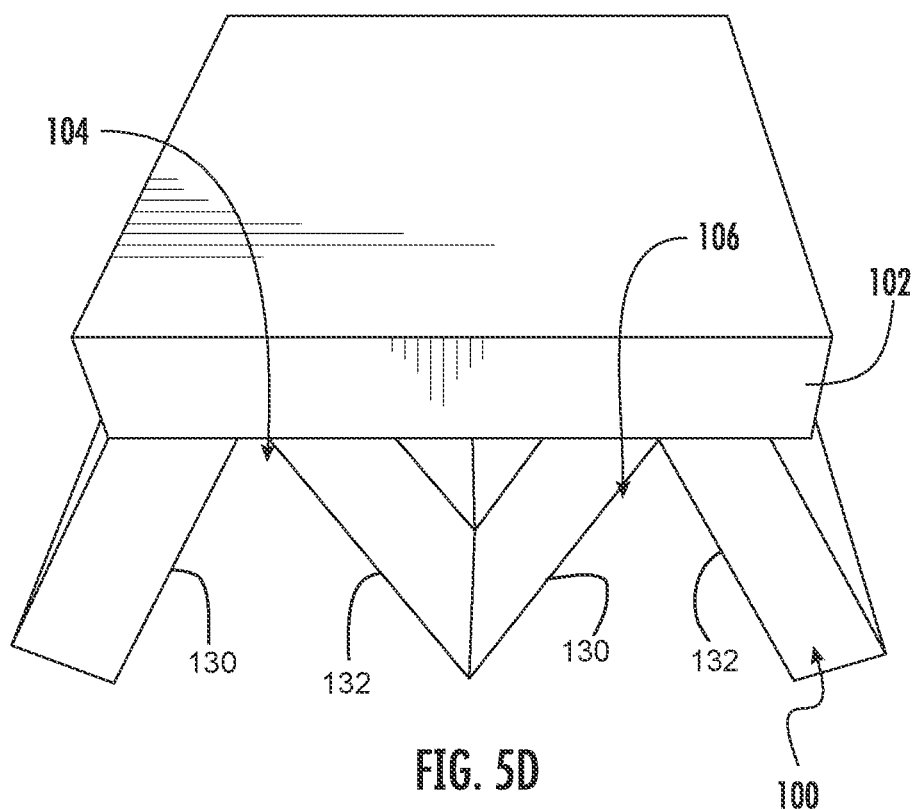
Figure 5E:
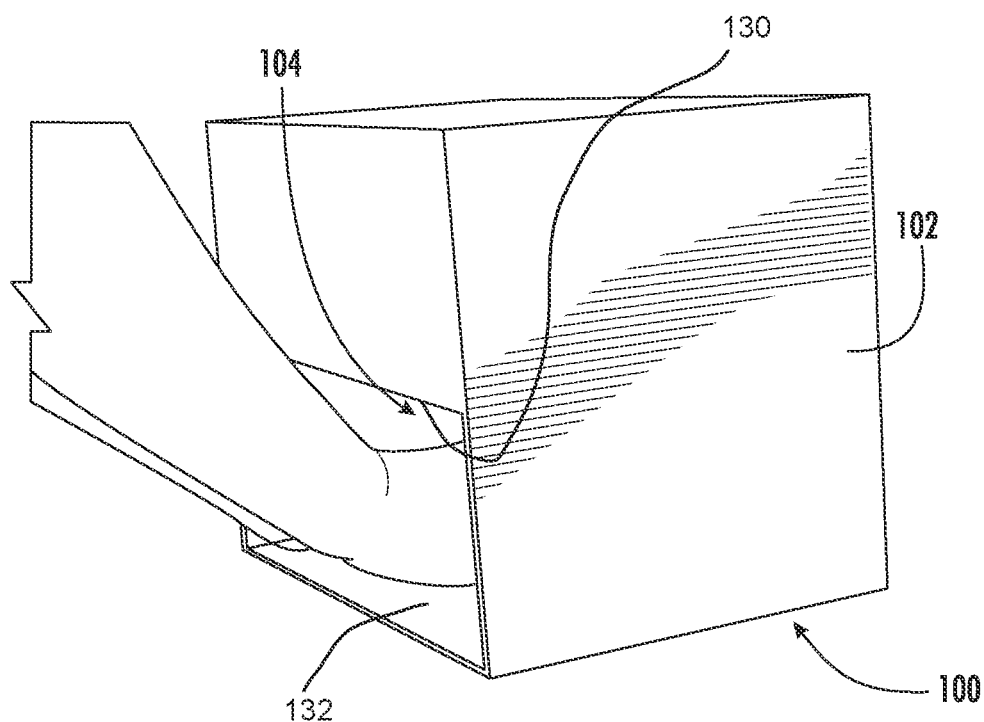
Figure 5F:
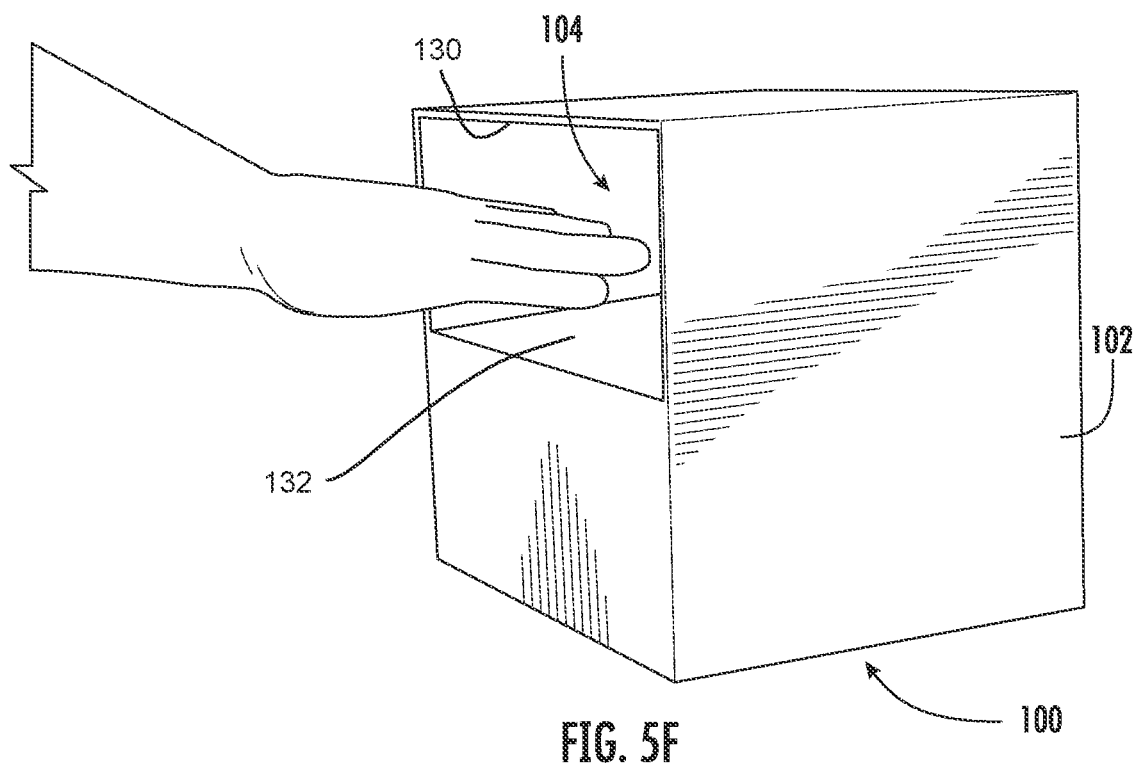
Figure 5G:
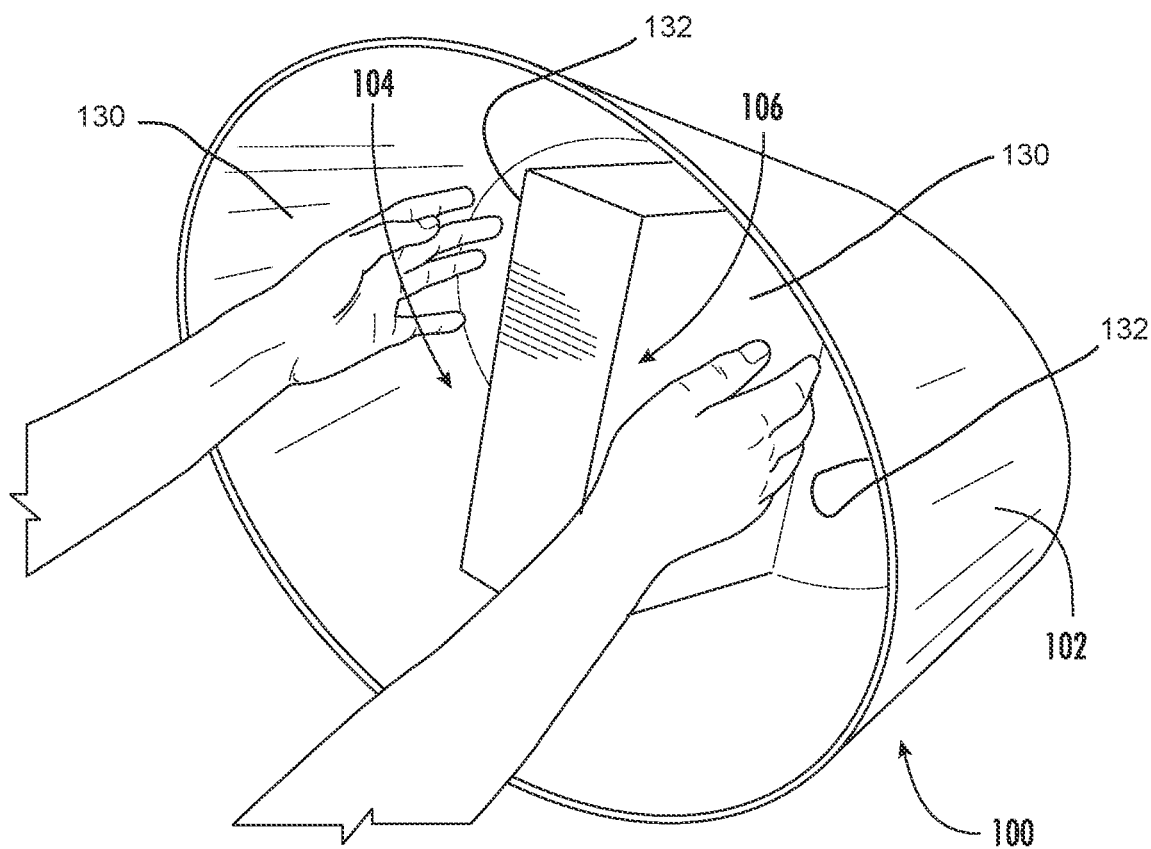
Figure 5H:
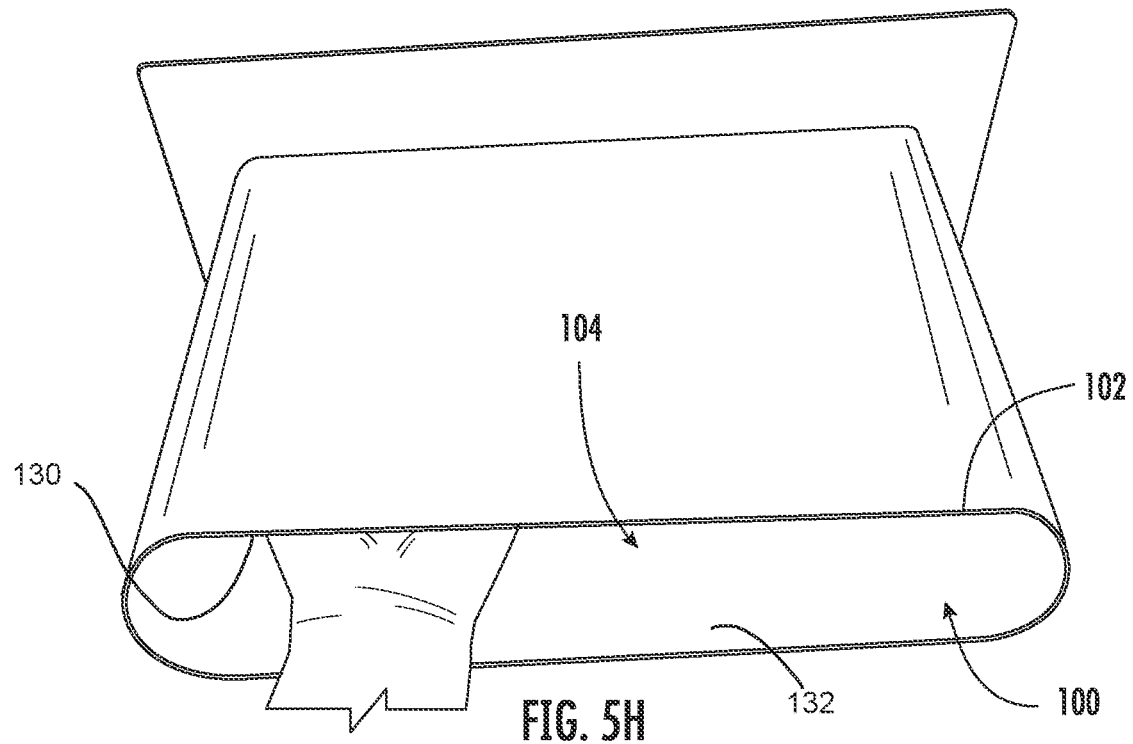
Figure 5I:
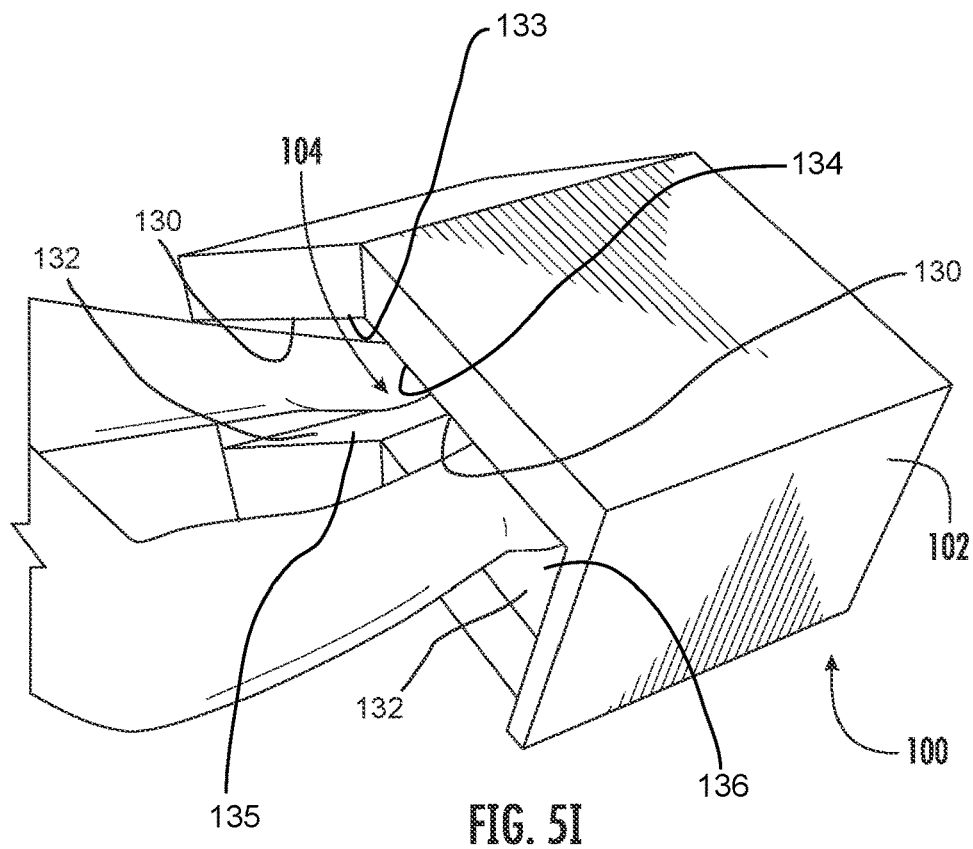
Figure 5J:
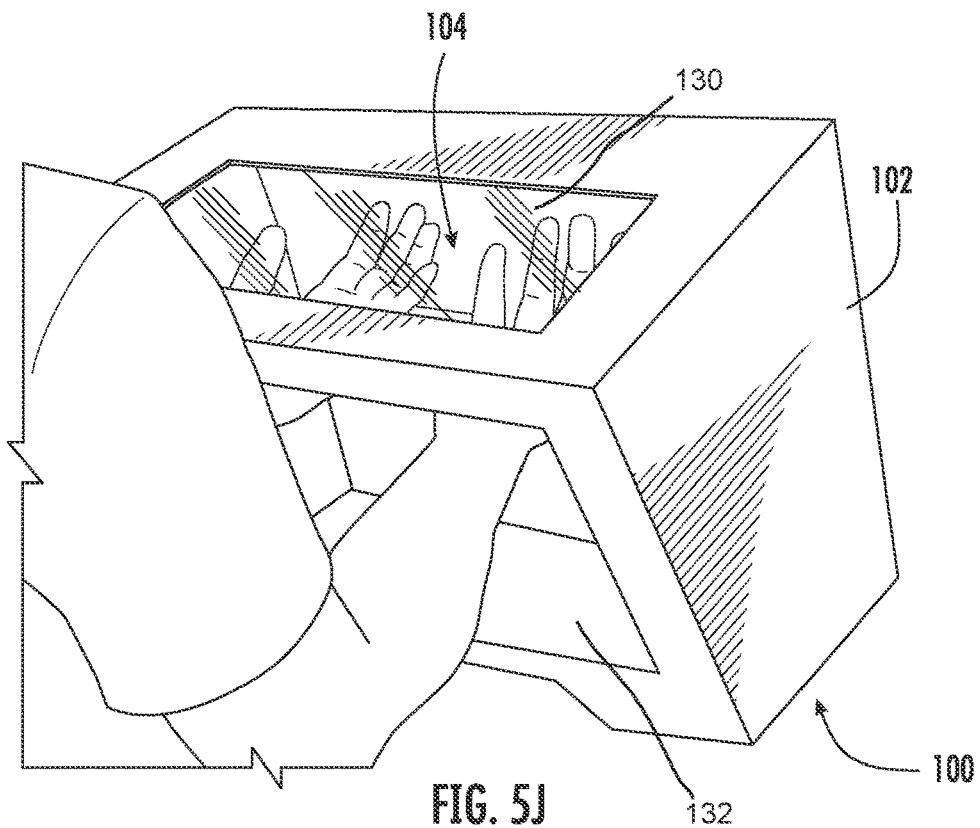
Figure 5K:
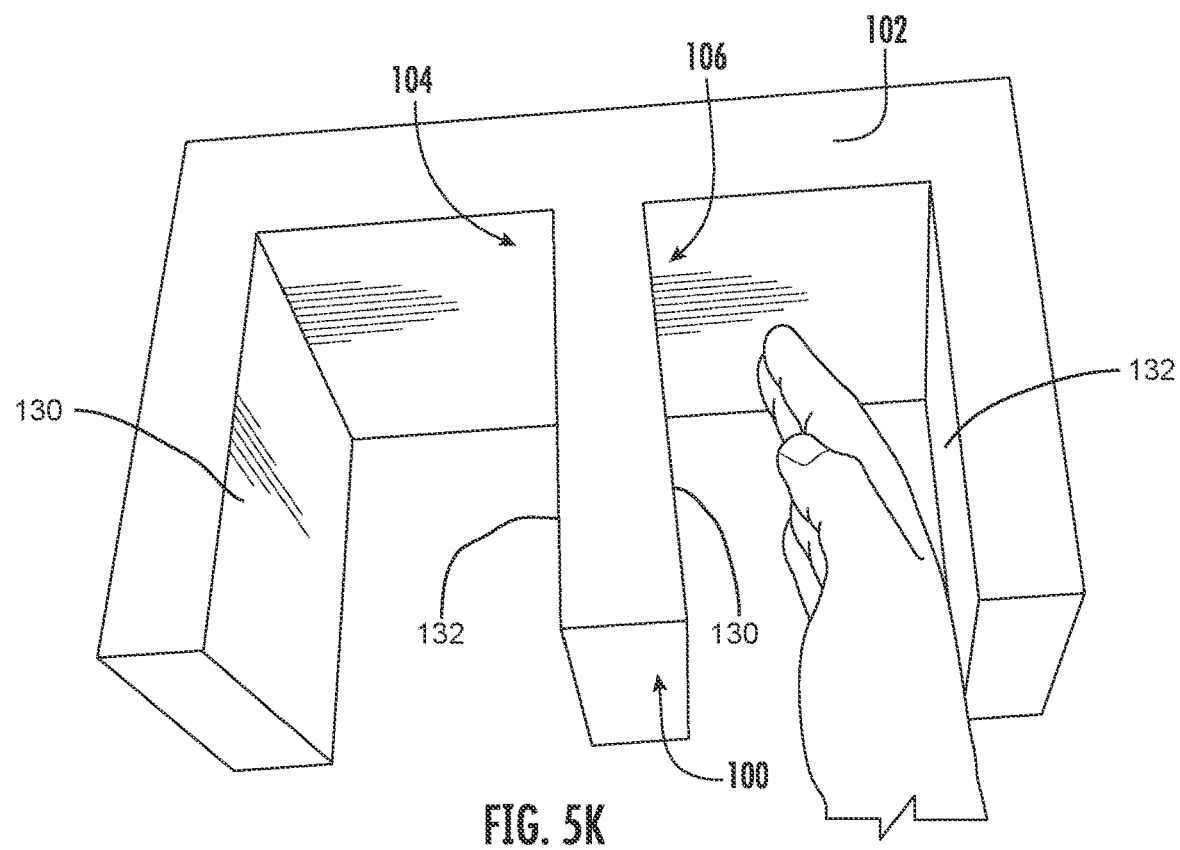
Figure 5L:
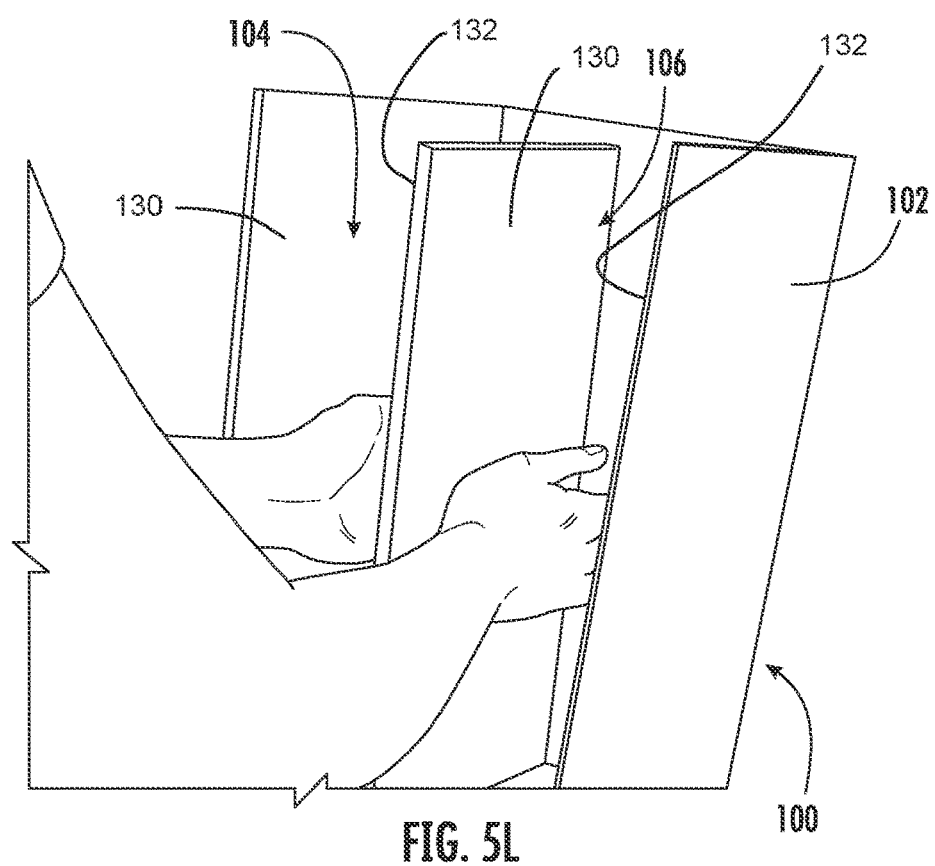
Figure 5M:
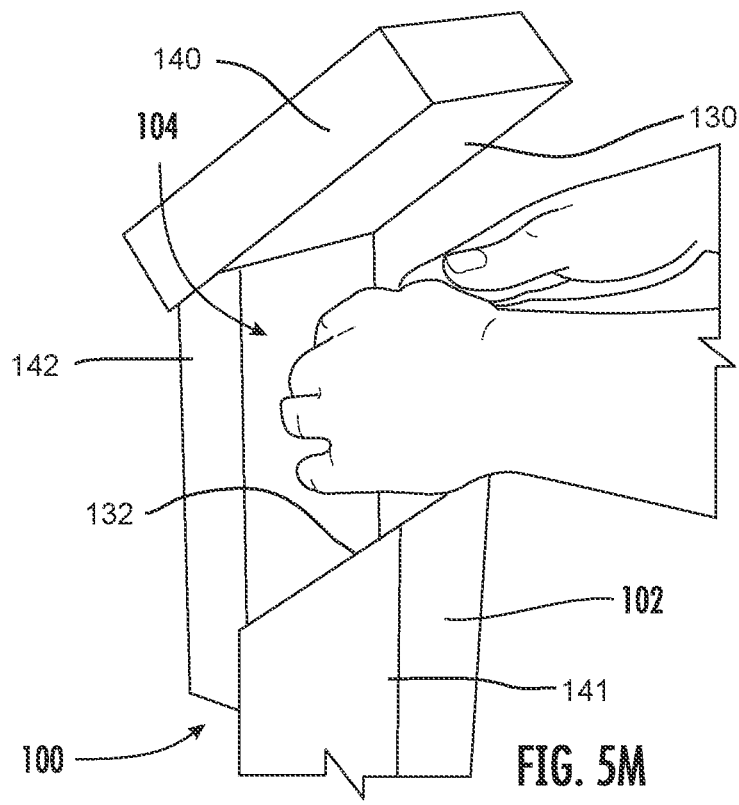
Figure 5N:
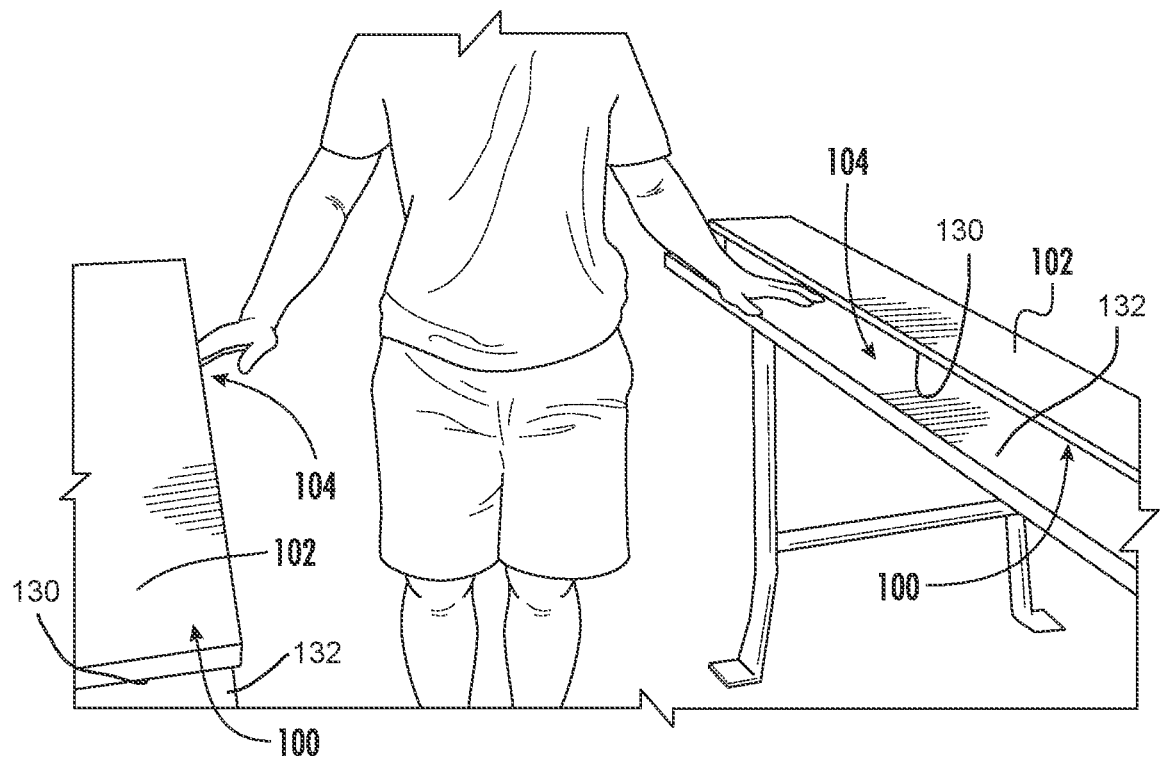
Figure 5O:
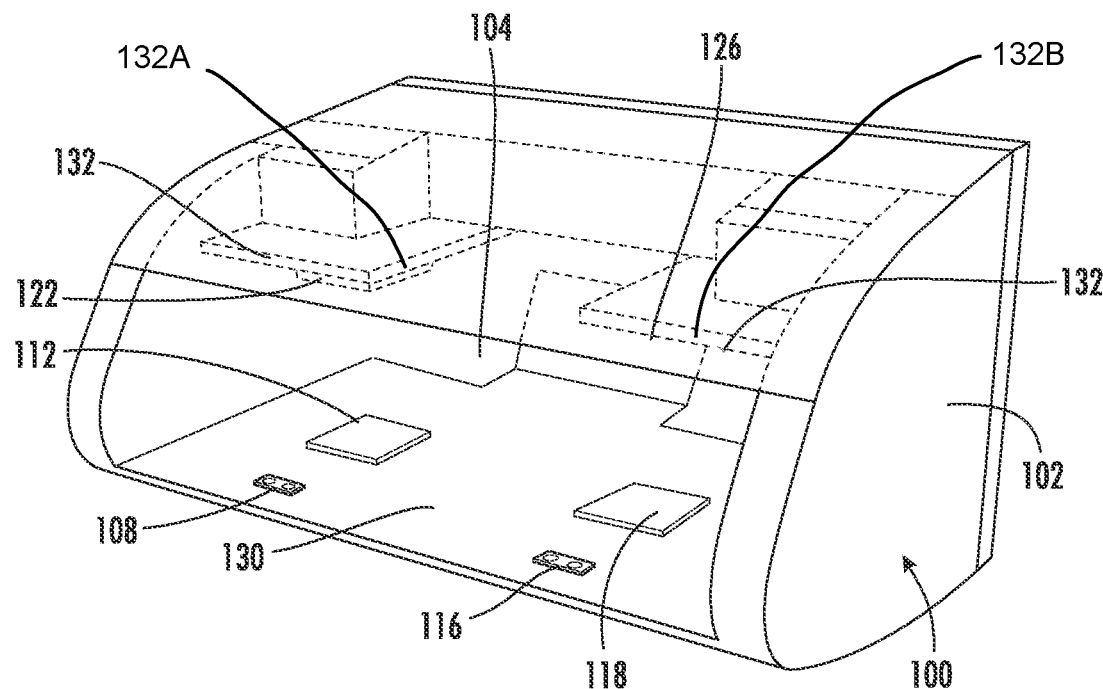
Figure 5P:
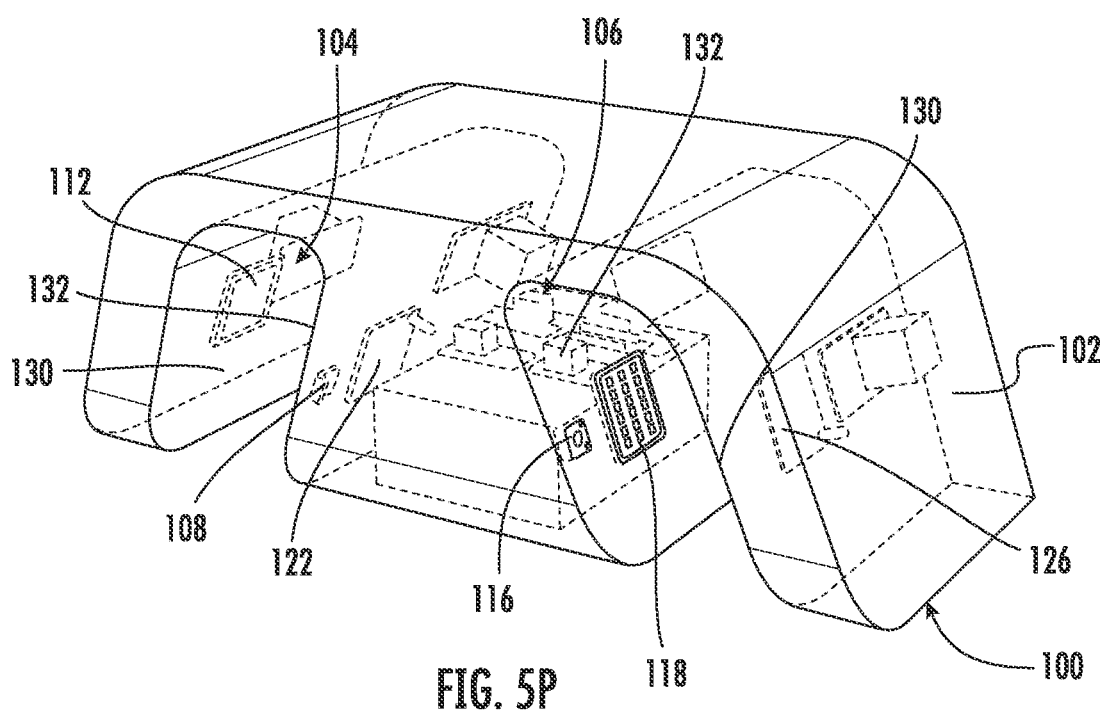

FIGS. 5A-5P illustrate additional embodiments of hand sanitizing devices 100 according to one or more aspects of the disclosure. The bodies 102 of the hand sanitizing devices 100 of FIGS. 5A-5P are designed and configured differently than the bodies 102 illustrated in FIGS. 1-2. It is understood that many of the devices 100 in FIGS. 5A-5P are depicted generally and schematically, to depict the shape and configuration of the body 102 in these embodiments. Specific components such as sensors and light arrays are not depicted in FIGS. 5A-5N, but one skilled in the art would clearly understand the positioning and functioning of these components in the bodies 102 of FIGS. 5A-5N based on the disclosures of other embodiments herein. For example, light arrays may be positioned on opposed or confronting surfaces 130, 132 defining a cavity or space 104 to receive a user's hands, and a sensor may also be positioned on such surfaces 130, 132 or elsewhere permitting the sensor to be directed into the cavity 104, as described herein with respect to other embodiments. Likewise, the hand sanitizing devices 100 of FIGS. 5A-5P may also include one or more electronic controllers as described herein. Additionally, some of the sanitizing devices 100 in FIGS. 5A-5P may have only a single cavity 104 configured to receive one or both of the user's hands. The devices 100 in FIGS. 5A-5P may be provided with any features and aspects described herein with respect to other embodiments, and may function in the same manner described herein.

FIG. 5A illustrates a system including a hand sanitizing device 100 with a body 102 having two cavities or spaces 104, 106, each configured to receive one of the user's hands. As similarly described herein with respect to the embodiment of FIG. 1, the body 102 includes at least a first surface 130 and a second surface 132 defining each of the cavities 104, 106, where the first and second surfaces 130, 132 oppose or confront each other, and each surface 130, 132 may have at least one light array (not shown) mounted thereon, as described herein. Each cavity 104, 106 may also have a sensor (not shown) configured to sense the presence of a user's hand(s) in the respective cavity 104, 106, as also described herein. The surfaces 130, 132 defining each cavity 104, 106 in this embodiment are oriented vertically and parallel to each other. The body 102 in FIG. 5A is configured for a free-standing configuration such that the cavities 104, 106 open upward, but the body 102 may be arranged for a different free-standing orientation, or for a wall mount or other configuration, in other embodiments.

FIG. 5B illustrates a system including a hand sanitizing device 100 with a body 102 having two cavities or spaces 104, 106, each configured to receive one of the user's hands. As similarly described herein with respect to the embodiment of FIG. 1, the body 102 includes at least a first surface 130 and a second surface 132 defining each of the cavities 104, 106, where the first and second surfaces 130, 132 oppose or confront each other, and each surface 130, 132 may have at least one light array (not shown) mounted thereon, as described herein. Each cavity 104, 106 may also have a sensor (not shown) configured to sense the presence of a user's hand(s) in the respective cavity 104, 106, as also described herein. The surfaces 130, 132 defining each cavity 104, 106 in this embodiment are oriented vertically and parallel to each other. The body 102 in FIG. 5B is configured for a free-standing configuration such that the cavities 104, 106 open downward, but the body 102 may be arranged for a different free-standing orientation, or for a wall mount or other configuration, in other embodiments.

FIG. 5C illustrates a system including a hand sanitizing device 100 with a body 102 having two cavities or spaces 104, 106, each configured to receive one of the user's hands. As similarly described herein with respect to the embodiment of FIG. 1, the body 102 includes at least a first surface 130 and a second surface 132 defining each of the cavities 104, 106, where the first and second surfaces 130, 132 oppose or confront each other, and each surface 130, 132 may have at least one light array (not shown) mounted thereon, as described herein. Each cavity 104, 106 may also have a sensor (not shown) configured to sense the presence of a user's hand(s) in the respective cavity 104, 106, as also described herein. The surfaces 130, 132 defining each cavity 104, 106 in this embodiment are oriented vertically and parallel to each other. Additionally, the surfaces 130, 132 defining one cavity 104 are obliquely and acutely angled to the surfaces 130, 132 defining the other cavity 106. The body 102 in FIG. 5C is configured for mounting to a wall surface such that the cavities 104, 106 open upward, but the body 102 may be arranged for wall mounting in a different orientation, or for a free-standing or other configuration, in other embodiments.

FIG. 5D illustrates a system including a hand sanitizing device 100 with a body 102 having two cavities or spaces 104, 106, each configured to receive one of the user's hands. As similarly described herein with respect to the embodiment of FIG. 1, the body 102 includes at least a first surface 130 and a second surface 132 defining each of the cavities 104, 106, where the first and second surfaces 130, 132 oppose or confront each other, and each surface 130, 132 may have at least one light array (not shown) mounted thereon, as described herein. Each cavity 104, 106 may also have a sensor (not shown) configured to sense the presence of a user's hand(s) in the respective cavity 104, 106, as also described herein. The surfaces 130, 132 defining each cavity 104, 106 in this embodiment are oriented at an acute angle to each other and toward the vertical direction, such that the cavity 104, 106 is wider at the open end and narrower at the opposite end (i.e., distal from the open end). In one embodiment, the surfaces 130, 132 are angled from 5 degrees to 15 degrees with respect to the vertical direction, or from 10 degrees to 30 degrees with respect to each other. In another embodiment, these angles may be approximately 10 degrees and 20 degrees, respectfully. The body 102 in FIG. 5D is configured for mounting to a wall surface such that the cavities 104, 106 open downward, but the body 102 may be arranged for wall mounting in a different orientation, or for a free-standing or other configuration, in other embodiments.

FIGS. 5E and 5F illustrate embodiments of a system including a hand sanitizing device 100 with a body 102 having a cavity or space 104 configured to receive one or both of the user's hands. As similarly described herein with respect to the embodiment of FIG. 1, the body 102 in each of these embodiments includes at least a first surface 130 and a second surface 132 defining the cavity 104, where the first and second surfaces 130, 132 oppose or confront each other, and each surface 130, 132 may have at least one light array (not shown) mounted thereon, as described herein. Each cavity 104, 106 may also have a sensor (not shown) configured to sense the presence of a user's hand(s) in the respective cavity 104, 106, as also described herein. The surfaces 130, 132 defining the cavity 104 in FIGS. 5E and 5F are oriented horizontal and parallel to each other. The bodies 102 in FIGS. 5E and 5F are each configured for a free-standing configuration such that the cavity 104 opens forward, but the body 102 may be arranged for a different free-standing orientation, or for a wall mount or other configuration, in other embodiments. The body 102 in FIG. 5E has the cavity 104 positioned near a top of the body 102, and the body 102 in FIG. 5G has the cavity 104 positioned near a top of the body 102.

FIG. 5G illustrates a system including a hand sanitizing device 100 with a body 102 having two cavities or spaces 104, 106, each configured to receive one of the user's hands. As similarly described herein with respect to the embodiment of FIG. 1, the body 102 includes at least a first surface 130 and a second surface 132 defining each of the cavities 104, 106, where the first and second surfaces 130, 132 oppose or confront each other, and each surface 130, 132 may have at least one light array (not shown) mounted thereon, as described herein. Each cavity 104, 106 may also have a sensor (not shown) configured to sense the presence of a user's hand(s) in the respective cavity 104, 106, as also described herein. The surfaces 130, 132 defining the cavities 104, 106 in this embodiment include rounded surfaces 130 that are curved around the insides of the peripheries of the cavities 104, 106, and flat surfaces 132 in the center that are oriented vertically and face outward into the cavities 104, 106. The body 102 in FIG. 5G is configured for mounting to a wall surface such that the cavities 104, 106 open outward, but the body 102 may be arranged for wall mounting in a different orientation, or for a free-standing or other configuration, in other embodiments.

FIG. 5H illustrates a system including a hand sanitizing device 100 with a body 102 having a cavity or space 104 configured to receive one or both of the user's hands. As similarly described herein with respect to the embodiment of FIG. 1, the body 102 includes at least a first surface 130 and a second surface 132 defining the cavity 104, where the first and second surfaces 130, 132 oppose or confront each other, and each surface 130, 132 may have at least one light array (not shown) mounted thereon, as described herein. The cavity 104 may also have a sensor (not shown) configured to sense the presence of a user's hand(s) in the cavity 104, as also described herein. The surfaces 130, 132 defining the cavity 104 in FIG. 5H are oriented horizontal and parallel to each other. The body 102 in FIG. 5H is configured for mounting to a wall surface such that the cavity 104 opens outward, but the body 102 may be arranged for wall mounting in a different orientation, or for a free-standing or other configuration, in other embodiments.

FIG. 5I illustrates a system including a hand sanitizing device 100 with a body 102 having a cavity or space 104 configured to receive one or both of the user's hands. As similarly described herein with respect to the embodiment of FIG. 1, the body 102 includes at least a first surface 130 and a second surface 132 defining each of the cavities 104, 106, where the first and second surfaces 130, 132 oppose or confront each other, and each surface 130, 132 may have at least one light array (not shown) mounted thereon, as described herein. The cavity 104 may also have a sensor (not shown) configured to sense the presence of a user's hand(s) in the cavity 104, as also described herein. The surfaces 130, 132 defining the cavity 104 in this embodiment include two surface portions 133, 134, 135, 136 that are obliquely and obtusely angled with respect to each other, with pairs of opposing surface portions 133, 134, 135, 136 oriented parallel to each other. The body 102 in FIG. 5I is configured for mounting to a wall surface such that the cavity 104 opens outward, but the body 102 may be arranged for wall mounting in a different orientation, or for a free-standing or other configuration, in other embodiments.

FIG. 5J illustrates a system including a hand sanitizing device 100 with a body 102 having a cavity or space 104 configured to receive one or both of the user's hands. As similarly described herein with respect to the embodiment of FIG. 1, the body 102 includes at least a first surface 130 and a second surface 132 defining the cavity 104, where the first and second surfaces 130, 132 oppose or confront each other, and each surface 130, 132 may have at least one light array (not shown) mounted thereon, as described herein. The cavity 104 may also have a sensor (not shown) configured to sense the presence of a user's hand(s) in the cavity 104, as also described herein. The surfaces 130, 132 defining the cavity 104 in this embodiment are parallel with respect to each other. The first surface 130 may be at least partially formed of a transparent or translucent material in this embodiment, in order to permit the user to view the positioning of the hand(s) within the cavity 104. The body 102 in FIG. 5J is configured for mounting to a wall surface such that the cavity 104 opens outward, but the body 102 may be arranged for wall mounting in a different orientation, or for a free-standing or other configuration, in other embodiments. The body 102 in FIG. 5J is narrower at the bottom and wider at the top, so the cavity 104 is angled slightly downward, and the user can insert their hands at an upward angle into the cavity 104.

FIG. 5K illustrates a system including a hand sanitizing device 100 with a body 102 having two cavities or spaces 104, 106, each configured to receive one of the user's hands. As similarly described herein with respect to the embodiment of FIG. 1, the body 102 includes at least a first surface 130 and a second surface 132 defining each of the cavities 104, 106, where the first and second surfaces 130, 132 oppose or confront each other, and each surface 130, 132 may have at least one light array (not shown) mounted thereon, as described herein. Each cavity 104, 106 may also have a sensor (not shown) configured to sense the presence of a user's hand(s) in the respective cavity 104, 106, as also described herein. The surfaces 130, 132 defining each cavity 104, 106 in this embodiment are oriented vertically and parallel to each other. The body 102 in FIG. 5K is configured for a free-standing configuration such that the cavities 104, 106 open horizontally outward toward the user, but the body 102 may be arranged for a different free-standing orientation, or for a wall mount or other configuration, in other embodiments.

FIG. 5L illustrates a system including a hand sanitizing device 100 with a body 102 having two cavities or spaces 104, 106, each configured to receive one of the user's hands. As similarly described herein with respect to the embodiment of FIG. 1, the body 102 includes at least a first surface 130 and a second surface 132 defining each of the cavities 104, 106, where the first and second surfaces 130, 132 oppose or confront each other, and each surface 130, 132 may have at least one light array (not shown) mounted thereon, as described herein. Each cavity 104, 106 may also have a sensor (not shown) configured to sense the presence of a user's hand(s) in the respective cavity 104, 106, as also described herein. The surfaces 130, 132 defining each cavity 104, 106 in this embodiment are oriented vertically and parallel to each other. The body 102 in FIG. 5L is configured for mounting to a wall surface such that the cavities 104, 106 open horizontally outward toward the user, but the body 102 may be arranged for a different wall mount orientation, or for a free-standing or other configuration, in other embodiments.

FIG. 5M illustrates a system including a hand sanitizing device 100 with a body 102 having a cavity or space 104 configured to receive one or both of the user's hands. As similarly described herein with respect to the embodiment of FIG. 1, the body 102 includes at least a first surface 130 and a second surface 132 defining the cavity 104, where the first and second surfaces 130, 132 oppose or confront each other and face into the cavity 104, and each surface 130, 132 may have at least one light array (not shown) mounted thereon, as described herein. The cavity 104 may also have a sensor (not shown) configured to sense the presence of a user's hand(s) in the cavity 104, as also described herein. The surfaces 130, 132 defining the cavity 104 in FIG. 5M are oriented parallel to each other and obliquely and acutely angled with respect to a horizontal plane. The body 102 in FIG. 5M includes an upper portion 140 having the first surface 130 as a bottom surface thereof and a lower portion 141 having the second surface 132 as a top surface thereof, with an arm 142 connecting the upper portion 140 and the lower portion 141 and extending vertically between the upper and lower portions 140, 141. The body 102 in FIG. 5M is configured for mounting to a wall surface such that the cavity 104 opens outward, but the body 102 may be arranged for wall mounting in a different orientation, or for a free-standing or other configuration, in other embodiments. The cavity 104 in FIG. 5M is angled slightly upward, and the user can insert their hands at a downward angle into the cavity 104.

FIG. 5N illustrates a system including two hand sanitizing devices 100 with bodies 102 arranged as a pair of elongated hand rails that can be mounted to wall surfaces or in free-standing configurations. As similarly described herein with respect to the embodiment of FIG. 1, each body 102 includes at least a first surface 130 and a second surface 132 defining a cavity or space 104, where the first and second surfaces 130, 132 oppose or confront each other, and each surface 130, 132 may have at least one light array (not shown) mounted thereon, as described herein. Each cavity 104 may also have a sensor (not shown) configured to sense the presence of a user's hand(s) in the respective cavity 104, as also described herein. The surfaces 130, 132 defining each cavity 104 in this embodiment are oriented horizontally and parallel to each other. The cavities 104 of the devices 100 in this embodiment are arranged as elongated slots that are configured to receive the user's hands as the user is passing between the hand rails, such that the user runs their hands along at least a portion of the lengths of the slots. Such a configuration may be provided at an entryway or exit to a building or room, to encourage sanitization by each person who enters and/or exits.

FIG. 5O illustrates an example embodiment of a hand sanitizing device 100 with a body 102 having a cavity or space 104 configured to receive one or both of the user's hands. As similarly described herein with respect to the embodiment of FIG. 1, the body 102 includes at least a first surface 130 and a second surface 132 defining the cavity 104, where the first and second surfaces 130, 132 oppose or confront each other, and each surface 130, 132 may have at least one light array mounted thereon, as described herein. Light arrays 112, 118, 122, 126 are shown in FIG. 5O. The cavity 104 may also have a sensor or sensors 108, 116 configured to sense the presence of a user's hand(s) in the cavity 104, as also described herein. The surfaces 130, 132 defining the cavity 104 in this embodiment are parallel with respect to each other. The top portion of the body 102 may be formed of a transparent or translucent material in this embodiment, in order to permit the user to view the positioning of the hand(s) within the cavity 104. Additionally, the second surface 132 is split into two different portions 132A, 132B that are spaced from each other to permit visibility of the hand(s) in the cavity 104, with each portion 132A, 132B having a light array 122, 126 thereon. The body 102 in FIG. 5O is configured for mounting to a wall surface such that the cavity 104 opens outward, but the body 102 may be arranged for wall mounting in a different orientation, or for a free-standing or other configuration, in other embodiments.

FIG. 5P illustrates an example embodiment of a hand sanitizing device 100 with a body 102 having two cavities or spaces 104, 106, each configured to receive one of the user's hands. As similarly described herein with respect to the embodiment of FIG. 1, the body 102 includes at least a first surface 130 and a second surface 132 defining each of the cavities 104, 106, where the first and second surfaces 130, 132 oppose or confront each other, and each surface 130, 132 may have at least one light array mounted thereon, as described herein. Light arrays 112, 118, 122, 126 are shown in FIG. 5P. Each cavity 104, 106 may also have a sensor or sensors 108, 116 configured to sense the presence of a user's hand(s) in the respective cavity 104, 106 as also described herein. The surfaces 130, 132 defining the cavities 104, 106 in this embodiment are parallel with respect to each other and are obliquely angled with respect to a vertical plane and with respect to the surfaces 130, 132 of the other cavity 104, 106. The body 102 in FIG. 5O is configured for mounting to a wall surface such that the cavities 104 open downward, but the body 102 may be arranged for wall mounting in a different orientation, or for a free-standing or other configuration, in other embodiments.

FIGS. 6A-6F show example embodiments of a hand sanitizing device 600 according to one or more aspects of the disclosure. The hand sanitizing device 600 may be a self-standing device, comprising an upper portion 602 and a lower portion 604 interconnected by an arm 606. The upper and lower portions 602, 604 in this embodiment are both cylindrical in shape, with a circular cross-section. In some examples, the hand sanitizing device 600 may be a column approximately sixty (60) inches tall with a six (6) inch diameter. It will be appreciated that these dimensions are merely illustrative and any suitable height and diameter may be used for the hand sanitizing device 600.

Figure 6A:
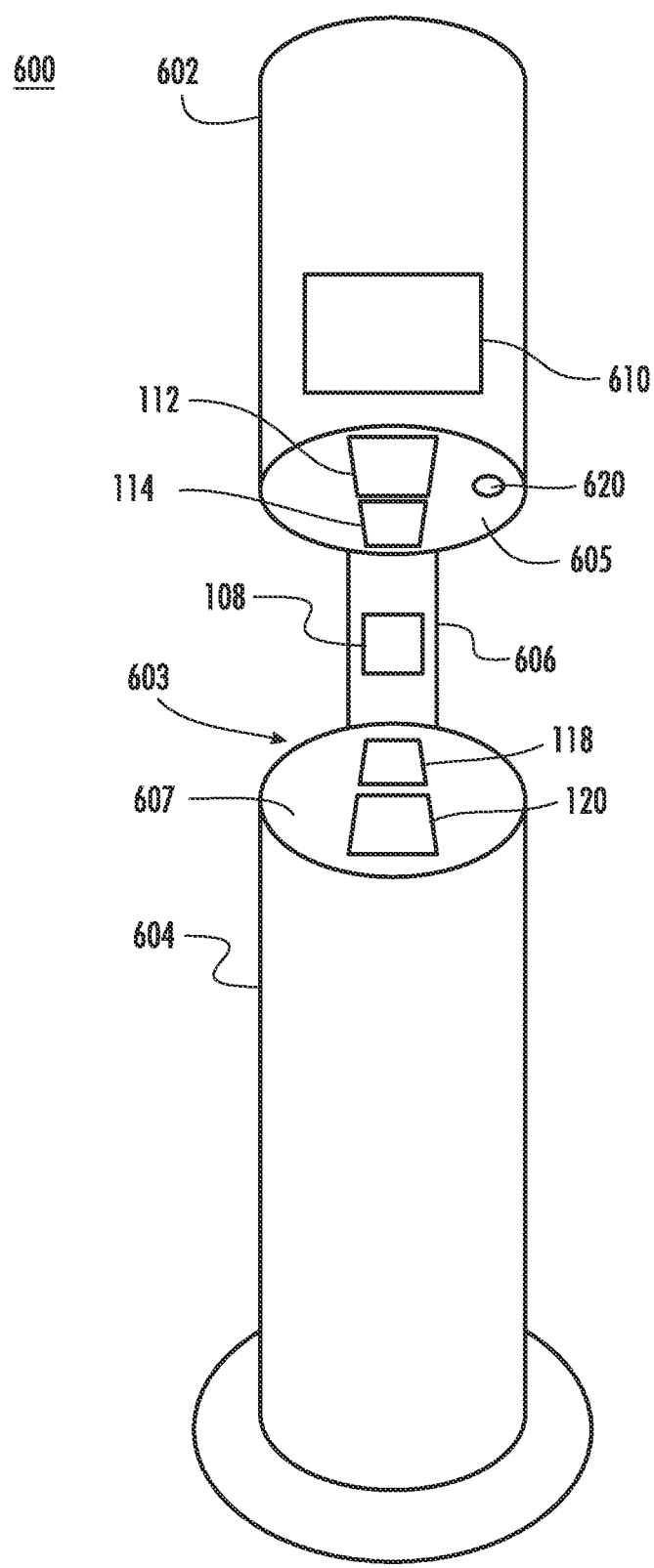
FIGS. 6A-6F show an example of a hand sanitizing device according to one or more aspects of the disclosure.

The device 600 may comprise a sensor 108, which may be positioned in, or on, the arm 606 in the embodiment of FIG. 6A. The sensor 108 may be configured to detect the presence, or absence, of human hands being placed in the space or cavity 603 formed between the bottom surface 605 of the upper portion 602 and the top surface 607 of the lower portion 604. The sensor 108 may have a 500 mm viewing distance in one embodiment, or a 200 mm viewing distance in another embodiment. For the configuration illustrated in FIG. 6A, the sensor 108 may have a vertical field of view of 45 degrees from the horizontal line of sight (e.g., 22.5 vertical degrees in each direction), or preferably, the vertical field of view may be 20 degrees from the horizontal line of sight (e.g., 10 vertical degrees in each direction). For the configuration in FIG. 6A, the horizontal field of view for the sensor 108 may be 90 degrees from the vertical line of sight (e.g., 45 degrees in each direction). It is understood that different fields of view may be used for other designs and configurations of the hand sanitizing device 600. Similar to the sensors described above, the sensor 108 may be an infrared (IR) sensor comprising one or more IR transmitters and one or more IR receivers. Additionally or alternatively, the sensor 108 may comprise a digital proximity, ambient light, RGB, and/or gesture sensor. The sensor 108 may comprise an IR LED and calibrated LED driver for gesture detection, proximity detection, ALS, and/or RGBC. The proximity detection feature may provide distance measurement (e.g., user's hand to sensor) by photodiode detection of reflected IR energy (sourced by the integrated LED). Additionally or alternatively, the sensor 108 may use time of flight technology to locate approaching users and/or detect hand movement. The Color and ALS detection feature may provide red, green, blue, and/or clear light intensity data. Each channel (e.g., R, G, B, C channels) may comprise a UV and/or IR blocking filter. The UV and/or IR blocking filter may allow the hand sanitizing device 600 to accurately measure ambient light and/or sense color which enables devices to calculate color temperature and/or control display backlight.

In addition to the sensor 108, the arm 606 may comprise one or more controllers (e.g., microcontrollers) and/or logic devices (e.g., ASIC, FPGAs, etc.) that control the operation of the hand sanitizing device 600. Such controller(s) and/or device(s) may be contained within the body of the arm 606. The one or more controllers and/or more logic device may send (e.g., transmit) a signal to a plurality of ultraviolet lights to activate the plurality of ultraviolet lights, for example, based on or in response to a signal received from the sensor 108 indicating that a user has placed their hands in the space formed between the upper portion 602 and the lower portion 604. The one or more controllers and/or logic devices may send (e.g., transmit) another signal to turn off the plurality of ultraviolet lights, for example, based on or in response to a signal received from the sensor 108 indicating that the user has removed their hands from the space formed between the upper portion 602 and the lower portion 604. The one or more controllers and/or logic devices may also be configured to turn the ultraviolet lights off after a set period of time after activation.

The hand sanitizing device 600 may include light emitting devices for emitting light (e.g., UV light) or other radiation appropriate for sanitization and/or sterilization of human skin. In one embodiment, the hand sanitizing device 600 may include at least one light array 112, 114 disposed on and/or supported by the upper portion 602, and at least one light array 118, 120 disposed on and/or supported by the lower portion 604. The hand sanitizing device 600 in the embodiment of FIG. 6A includes a first light array 112, a second light array 114, a display 610, and a sensor 620 all disposed on and/or supported by the upper portion 602. The first light array 112 and/or the second light array 114 may comprise any suitable light array configured to generate ultraviolet light in a wavelength safe for human tissue. The first light array 112 and/or the second light array 114 may be selected and/or oriented in order to cover ~95% of the contamination concentration areas on both the top and bottom of an outstretched human hand. This may be based on the average hand breadth, length, and/or circumference. The ultraviolet light generated by the first light array 112 and/or the second light array 114 may be 222 nm in one embodiment, which has proven effective for killing and/or destroying bacteria and viruses without being dangerous to humans and/or penetrating deeply into human cells. Alternatively, the ultraviolet light may have a different wavelength as described herein, in various embodiments. According to some examples, the hand sanitizing device 600 may comprise filters (not shown) over the first light array 112 and/or the second light array 114. The filters may restrict the wavelength of the ultraviolet light emitted by the first light array 112 and/or the second light array 114 to a desired wavelength for disinfection. In one embodiment, the filters may limit the wavelength of the ultraviolet light to 222 nm. It is understood that the wavelength of the light generated by the light arrays 112, 114 may be controlled by selective emission from the light array 112, 114, the use of filters as discussed herein, or both. It is noted that such filters may also provide safety for the user, by preventing emission of wavelengths of light that may cause skin damage or may otherwise be harmful. As noted above, the first light array 112 and/or the second light array 114 may comprise microplasma ultraviolet lamps, such as those manufactured by Eden Park Illumination. In another embodiment, the first light array 112 and/or the second light array 114 may comprise a plurality of ultraviolet light emitting diodes (LEDs) in a 50 mm (L)×50 mm (W)×3 mm (H) tile. Alternatively, the plurality of ultraviolet LEDs may be in a 125 mm (L)×50 mm (W)×3 mm (H) tile. The first light array 112 and/or the second light array 114 may be driven by one or more ballasts (not shown). While two light arrays are shown in FIG. 6A, it will be appreciated that additional, or fewer, light arrays may be used.

The hand sanitizing device 600 in some embodiments may include steady and/or variable indicators for conveying information regarding proper use of the hand sanitizing device 600. In some examples, one or more LED strips (not shown) may be placed on either side of the first light array 112 and/or the second light array 114. Additionally or alternatively, light strips may be placed on both sides of the first light array 112 and/or the second light array 114. The LED strips may be any colored LEDs. Preferably, the LED strips are blue LEDs. In this regard, the LED strips may project light between space formed by the upper portion 602 and the lower portion 604. This may provide an indication to a user of where to place their hands. Additionally or alternatively, the LED strips may change colors to convey messaging to the users. For example, blue LEDs may invite the user to insert their hands in the space formed between the upper portion 602 and the lower portion 604. Red LEDs may provide an indication that the sanitation/sterilization/cleaning process is ongoing and the user should not remove their hands. Yellow LEDs may provide an indication that the sanitation/sterilization/cleaning process is concluding soon. Green LEDs may provide an indication that the sanitation/sterilization/cleaning process has completed and the user may remove their hands from the space formed between the upper portion 602 and the lower portion 604.

The hand sanitizing device 600 may include a display 610 in some embodiments, for example, the display 610 disposed on and/or supported by the upper portion 602 in the embodiment of FIG. 6A. The display 610 may be any suitable display and/or monitor capable of presenting information associated with the hand sanitizing device 600. The information may comprise maintenance information, service information, and/or instructions on how to use the hand sanitizing device 600. The display 610 may comprise a liquid crystal display (LCD) display technology, a light emitting diode (LED) display technology, vacuum florescent display technology, and/or the like.

The sensor 620 may be any suitable input device that is capable of detecting a user's hand placement. In some examples, the sensor 620 may comprise a camera or other suitable image capture device. The camera may provide a real-time display of the user's hand, for example, via the display 610. In this regard, the display 610 may cause an overlay of a hand outline to be displayed to allow the user to determine the correct hand placement to ensure sanitation and/or sterilization of their hands.

The hand sanitizing device 600 in the embodiment of FIG. 6A further includes a third light array 118 and/or a fourth light array 120 disposed on and/or supported by the lower portion 604 of the hand sanitizing device 600. The third light array 118 and/or a fourth light array 120 may be any of the light arrays discussed above with respect to the first light array 112 and the second light array 114. In some examples, the hand sanitizing device 600 may comprise one or more sensors (not shown) to detect the cleanliness of the plurality of light arrays 112, 114, 118, 120, which may be positioned within or adjacent to the light arrays 112, 114, 118, 120 in one embodiment, or elsewhere (e.g., on the arm 606) in another embodiment. The one or more sensors may be configured to detect an amount of ultraviolet light being emitted by the plurality of light arrays. If the amount of ultraviolet light falls below a predetermined threshold, the one or more sensors may send a signal that the plurality of ultraviolet lights need to be cleaned, or otherwise serviced.

Figure 6B:
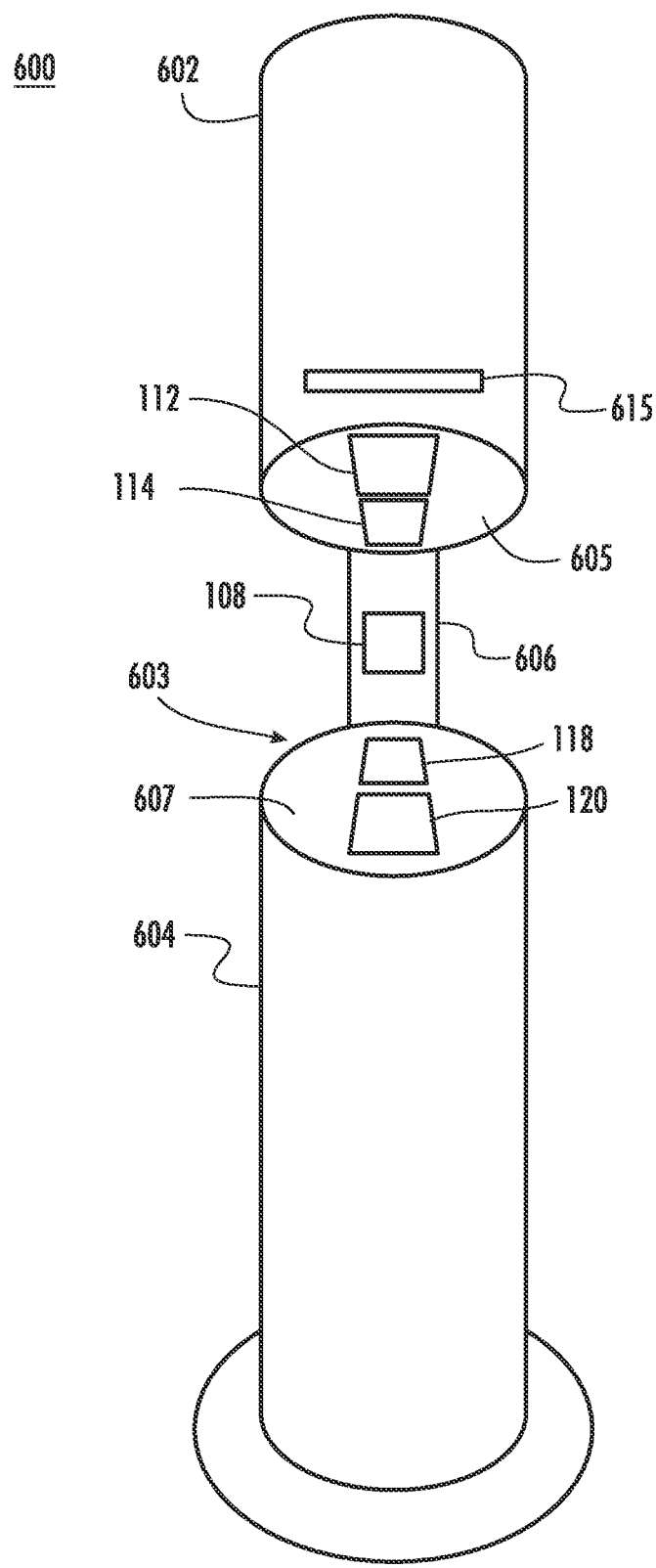
Figure 6C:
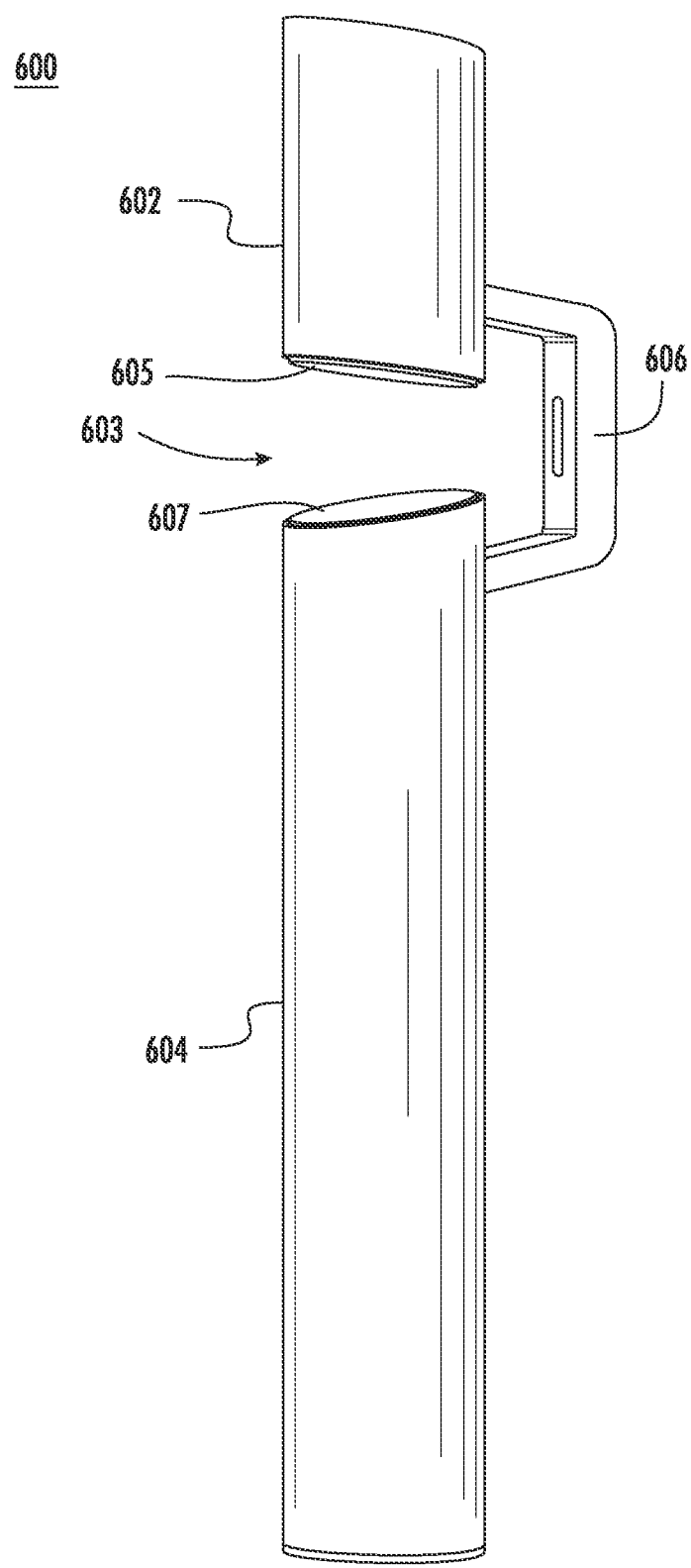
Figure 6D:
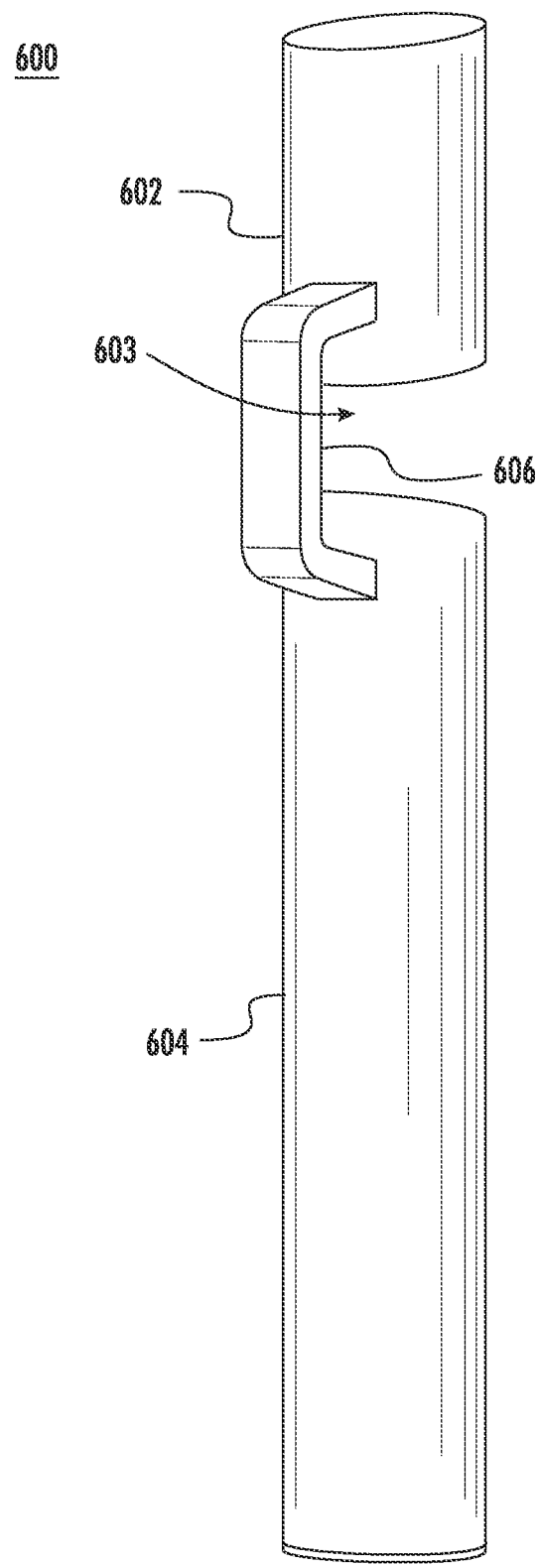

FIG. 6B shows an embodiment of a hand sanitizing device 600 that is similar to the embodiment of FIG. 6A in most aspects. In FIG. 6B, the display located in the upper portion 602 may be replaced with a human-readable output 615, such as an LED array or a speaker. The human-readable output 615 may use a plurality of light patterns, colors, sequences of light, sounds, noises, recordings, etc. to convey messages and/or signals to owners, maintenance, and/or users. This may allow the owners and/or maintenance to service, or otherwise maintain, the hand sanitizing device 600. Moreover, the human-readable output 615 may provide a better user experience by conveying the messages and/or signals to the user about the status of the fixture and the components thereof. In some examples, the human-readable output 615 may present a time decrementing function that visually or audibly conveys a countdown until the hand sanitizing device 600 will turn off. Additionally or alternatively, the decrementing function may convey a countdown until the hand cleaning and/or sterilization is completed.

Figure 6E:
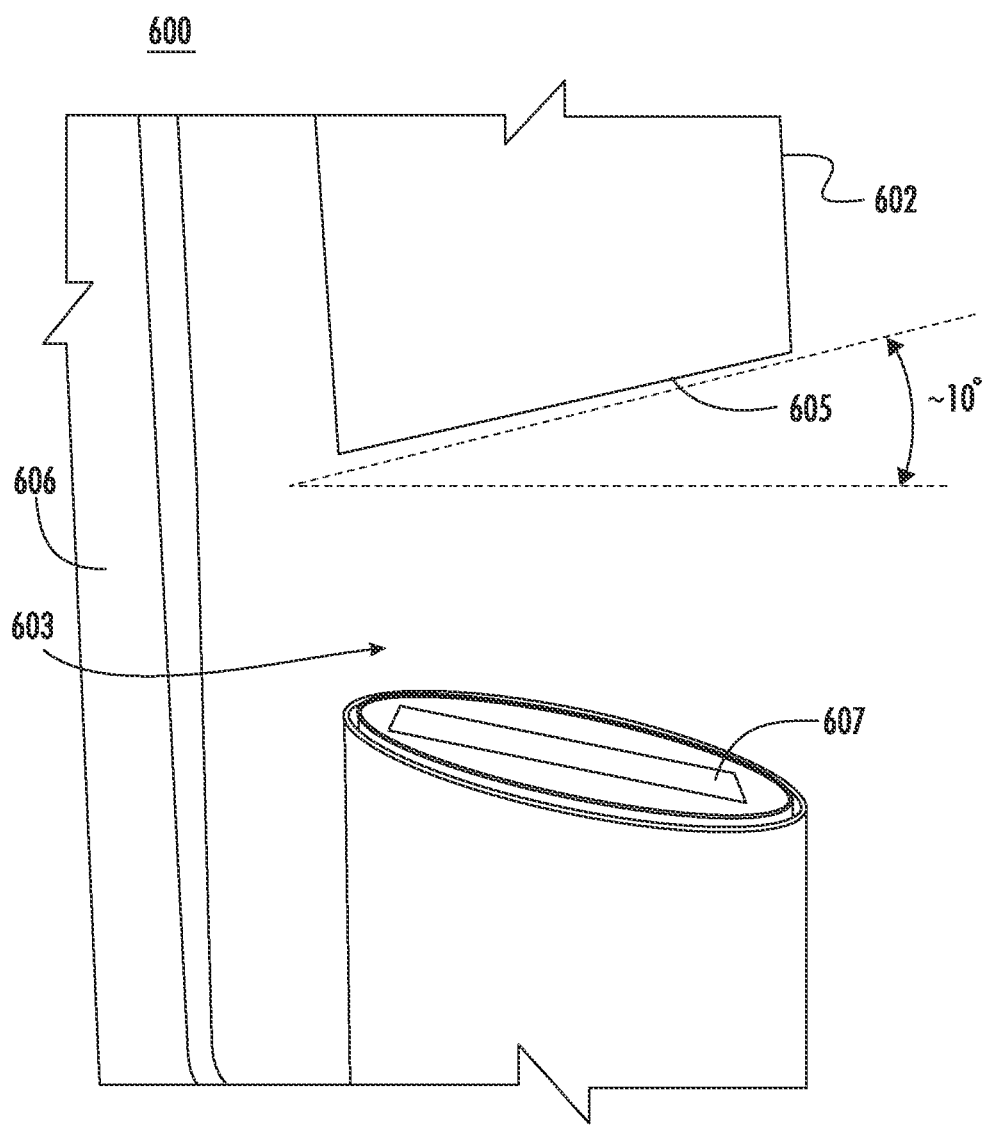
Figure 6F:
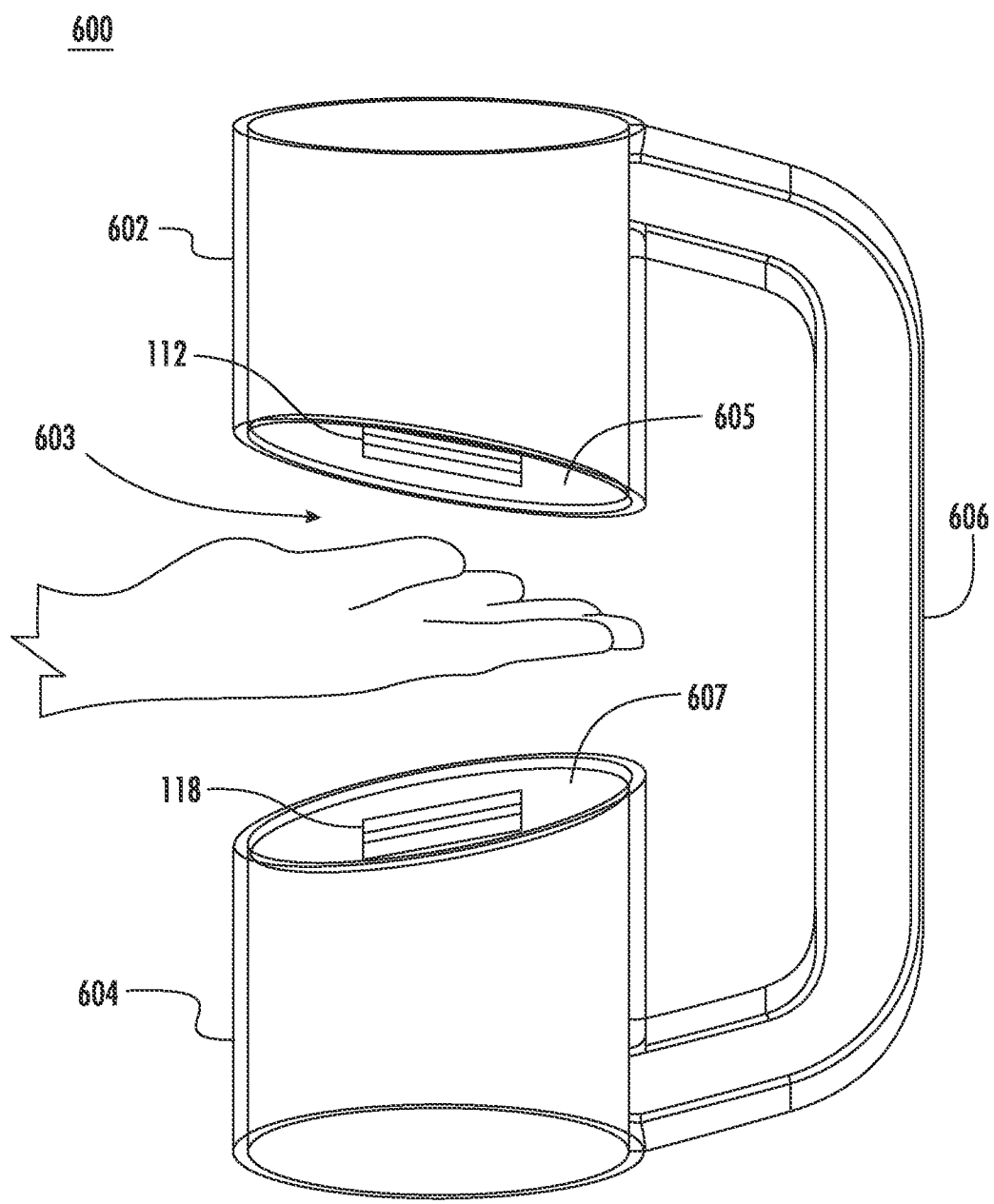

FIGS. 6C-6F show embodiments of the hand sanitizing device 600 that illustrate certain features from different perspectives. In one embodiment, as shown in FIGS. 6A-6F, the upper portion 602 and the lower portion 604 may have angled bottom and top surfaces 605, 607, respectively, confronting each other on opposite sides of the space 603 to form an opening that is more convenient and/or ergonomic to receive a user's hands. The bottom and top surfaces 605, 607 may be angled such that the space 603 is wider at the front of the hand sanitizing device 600 and narrower at the rear (i.e., proximate the arm 606). Both the surfaces 605, 607 are obliquely and acutely angled with respect to a horizontal plane and with respect to each other in the embodiment of FIGS. 6A-6F. In one embodiment, as shown in FIG. 6E, the angle for each surface 605, 607 is approximately 10 degrees with respect to a horizontal plane (or 20 degrees with respect to each other), and in another embodiment, the angle may be from 5 degrees to 15 degrees with respect to a horizontal plane (or 10-30 degrees with respect to each other). The light arrays 112, 114, 118, 120 may be disposed on or within the bottom and top surfaces 605, 607. FIG. 6F shows an example of the hand sanitizing device 600 with the proper hand positioning for hand sanitation and/or sterilization.

It will be appreciated that the apparatuses, methods, processes, and techniques described above may sanitize hands without the use of any liquids, such as soap and water or hand sanitizing fluids. The hand sanitizing device, and the techniques for using the hand sanitizing device, described herein may reduce the spread of infectious diseases, while providing an environmentally friendly solution that reduces water consumption and/or further reduces waste associated with drying towels.

One or more aspects discussed herein may be embodied in computer-usable or readable data and/or computer-executable instructions, such as in one or more program modules, executed by one or more computers or other devices as described herein. Generally, program modules include routines, programs, objects, components, data structures, and the like. that perform particular tasks or implement particular abstract data types when executed by a processor in a computer or other device. The modules may be written in a source code programming language that is subsequently compiled for execution, or may be written in a scripting language such as (but not limited to) HTML or XML. The computer executable instructions may be stored on a computer readable medium such as a hard disk, optical disk, removable storage media, solid-state memory, RAM, and the like. As will be appreciated by one of skill in the art, the functionality of the program modules may be combined or distributed as desired in various embodiments. In addition, the functionality may be embodied in whole or in part in firmware or hardware equivalents such as integrated circuits, field programmable gate arrays (FPGA), and the like. Particular data structures may be used to more effectively implement one or more aspects discussed herein, and such data structures are contemplated within the scope of computer executable instructions and computer-usable data described herein. Various aspects discussed herein may be embodied as a method, a computing device, a system, and/or a computer program product.

Various embodiments of hand sanitizing devices have been described herein, which include various components and features. In other embodiments, the hand sanitizing device may be provided with any combination of such components and features. It is also understood that in other embodiments, the various devices, components, and features of the hand sanitizing devices described herein may be constructed with similar structural and functional elements having different configurations, including different ornamental appearances.

Several alternative embodiments and examples have been described and illustrated herein. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. It is understood that the invention may be embodied in other specific forms without departing from the spirit or central characteristics thereof. The present examples and embodiments, therefore, are to be considered in all respects as illustrative and not restrictive, and the invention is not to be limited to the details given herein. The terms "top," "bottom," "front," "back," "side," "rear," and the like, as used herein, are intended for illustrative purposes only and do not limit the embodiments in any way. Nothing in this specification should be construed as requiring a specific three dimensional orientation of structures in order to fall within the scope of this invention, unless explicitly specified by the claims. When used in description of a method or process, the term "providing" (or variations thereof) as used herein means generally making an article available for further actions, and does not imply that the entity "providing" the article manufactured, assembled, or otherwise produced the article. The term "approximately" as used herein implies a variation of up to 10% of the nominal value modified by such term, or up to 10% of a midpoint value of a range modified by such term. Additionally, the term "plurality," as used herein, indicates any number greater than one, either disjunctively or conjunctively, as necessary, up to an infinite number. The term "oblique" or "obliquely angled," as used herein, indicates an angle that is not perpendicular (i.e., 90°) or straight (i.e., 180°). Accordingly, while the specific embodiments have been illustrated and described, numerous modifications come to mind without significantly departing from the spirit of the invention and the scope of protection is only limited by the scope of the accompanying claims.

What is claimed is:

1. A hand sanitizing device comprising:
a supporting body having a space configured to receive one or more hands of a user, the supporting body having a first surface and a second surface, with the space defined between the first and second surfaces, such that the first and second surfaces face into the space and are in confronting relation with each other, wherein the first surface and the second surface are angled at an acute angle with respect to each other;
a sensor mounted on the supporting body and directed into the space, the sensor being configured for sensing a presence of the one or more hands of the user within the space;
a first light array comprising a first plurality of light emitting devices mounted on the supporting body and configured to emit ultraviolet light from the first surface into the space;

a second light array comprising a second plurality of light emitting devices mounted on the supporting body and configured to emit ultraviolet light from the second surface into the space; and a controller mounted on the supporting body and connected to the sensor and the first and second light arrays, wherein the controller is configured to receive input from the sensor and to activate the first and second light arrays when the presence of the one or more hands of the user within the space is sensed by the sensor.

2. The hand sanitizing device of claim 1, wherein the acute angle is from 10 degrees to 30 degrees.

3. The hand sanitizing device of claim 1, wherein the supporting body has a second space configured to receive one or more hands of a user, the supporting body having a third surface and a fourth surface, with the second space defined between the third and fourth surfaces, such that the third and fourth surfaces face into the second space and are in confronting relation with each other.

4. The hand sanitizing device of claim 1, wherein the sensor is an infrared sensor comprising one or more infrared transmitters and one or more infrared receivers.

5. The hand sanitizing device of claim 4, wherein the sensor is a time of flight sensor.

6. The hand sanitizing device of claim 4, wherein the acute angle is from 10 degrees to 30 degrees, and the ultraviolet light emitted by the first plurality of light emitting devices and the second plurality of light emitting devices has a wavelength of 222 nm.

7. The hand sanitizing device of claim 6, further comprising a visual indicator mounted on the supporting body and configured to display a visual indication to the user related to operation of the hand sanitizing device.

8. The hand sanitizing device of claim 7, wherein the first light array further comprises a first filter positioned over the first plurality of light emitting devices and the second light array further comprises a second filter positioned over the second plurality of light emitting devices, wherein the first and second filters limit the wavelength of the ultraviolet light passing through the first and second filters to 222 nm.

9. A hand sanitizing device comprising:
a supporting body comprising a lower portion having a first surface and an upper portion having a second surface, with a space configured to receive one or more hands of a user, the space being defined between the first and second surfaces, such that the first and second surfaces face into the space and are in confronting relation with each other, the supporting body further comprising an arm connecting the lower portion to the upper portion and extending vertically from the lower portion to the upper portion;
a sensor mounted on the supporting body and directed into the space, the sensor being configured for sensing a presence of the one or more hands of the user within the space;
a first light array comprising a first plurality of light emitting devices mounted on the lower portion and configured to emit ultraviolet light from the first surface into the space;
a second light array comprising a second plurality of light emitting devices mounted on the upper portion and configured to emit ultraviolet light from the second surface into the space; and
a controller mounted on the supporting body and connected to the sensor and the first and second light arrays, wherein the controller is configured to receive input from the sensor and to activate the first and second light arrays when the presence of the one or more hands of the user within the space is sensed by the sensor.

10. The hand sanitizing device of claim 9, wherein the first surface and the second surface are angled at an acute angle with respect to each other.

11. The hand sanitizing device of claim 10, wherein the first surface and the second surface are angled at an acute angle with respect to each other.

12. The hand sanitizing device of claim 11, wherein the first surface and the second surface are angled at an acute angle with respect to each other, and wherein the acute angle is from 10 degrees to 30 degrees.

13. The hand sanitizing device of claim 9, further comprising a visual indicator mounted on the supporting body and configured to display a visual indication to the user related to operation of the hand sanitizing device.

14. The hand sanitizing device of claim 9, wherein the ultraviolet light emitted by the first plurality of light emitting devices and the second plurality of light emitting devices has a wavelength of 222 nm, wherein the first light array further comprises a first filter positioned over the first plurality of light emitting devices and the second light array further comprises a second filter positioned over the second plurality of light emitting devices, and wherein the first and second filters limit the wavelength of the ultraviolet light passing through the first and second filters to 222 nm.

15. The hand sanitizing device of claim 9, wherein the upper portion and the lower portion have circular cylindrical shapes.

16. The hand sanitizing device of claim 9, wherein the sensor is mounted on the arm and is directed into the space.

17. A hand sanitizing device comprising:
a supporting body comprising:
a lower portion having a top surface;
an upper portion having a bottom surface positioned directly above the top surface of the lower portion, wherein a space is defined between the top and bottom surfaces, such that the top and bottom surfaces face into the space and are in confronting relation with each other, wherein the space is configured to receive one or more hands of a user, and wherein the top surface and the bottom surface are angled at acute angles with respect to a horizontal plane; and
an arm connecting the lower portion to the upper portion and extending vertically from the lower portion to the upper portion;
a first light emitting device mounted on the lower portion and configured to emit ultraviolet light from the top surface into the space;
a second light emitting device mounted on the upper portion and configured to emit ultraviolet light from the bottom surface into the space; and
a sensor directed into the space, the sensor being configured for sensing a presence of the one or more hands of the user within the space.

18. The hand sanitizing device of claim 17, wherein the sensor is mounted on the arm and is directed into the space.

19. The hand sanitizing device of claim 17, further comprising a controller mounted on the supporting body and connected to the sensor and the first and second light emitting devices, wherein the controller is configured to receive input from the sensor and to activate the first and second light emitting devices when the presence of the one or more hands of the user within the space is sensed by the sensor.

20. The hand sanitizing device of claim 17, further comprising a first filter positioned over the first light emitting device and a second filter positioned over the second light emitting device, wherein the first and second filters limit a wavelength of the ultraviolet light passing through the first and second filters, and wherein the first filter forms a portion of the top surface, and the second filter forms a portion of the bottom surface.

21. The hand sanitizing device of claim 17, wherein the top and bottom surfaces are angled at an acute angle of 10 degrees to 30 degrees with respect to each other.

* * * * *